United States Patent
Wenderow et al.

(10) Patent No.: US 11,832,904 B2
(45) Date of Patent: Dec. 5, 2023

(54) ROBOTIC CATHETER SYSTEM WITH VARIABLE DRIVE MECHANISM

(71) Applicant: Corindus, Inc., Waltham, MA (US)

(72) Inventors: Tal Wenderow, Newton, MA (US); John Murphy, North Reading, MA (US)

(73) Assignee: Corindus, Inc., Newton, MA (US)

( * ) Notice: Subject to any disclaimer, the term of this patent is extended or adjusted under 35 U.S.C. 154(b) by 669 days.

(21) Appl. No.: 17/065,268

(22) Filed: Oct. 7, 2020

(65) Prior Publication Data

US 2021/0030492 A1 Feb. 4, 2021

Related U.S. Application Data

(63) Continuation of application No. 15/820,753, filed on Nov. 22, 2017, now Pat. No. 10,835,329, which is a
(Continued)

(51) Int. Cl.
*A61B 34/30* (2016.01)
*A61B 34/37* (2016.01)
(Continued)

(52) U.S. Cl.
CPC .............. *A61B 34/30* (2016.02); *A61B 34/37* (2016.02); *A61B 2017/0046* (2013.01);
(Continued)

(58) Field of Classification Search
CPC .. A61B 2017/0046; A61B 2017/00469; A61B 2034/301; A61B 2034/303;
(Continued)

(56) References Cited

U.S. PATENT DOCUMENTS

| | | | |
|---|---|---|---|
| 5,720,742 A * | 2/1998 | Zacharias | A61B 17/29 606/1 |
| 5,821,920 A | 10/1998 | Rosenberg et al. | |
| 6,264,630 B1 | 7/2001 | Mickley et al. | |
| 6,375,471 B1 * | 4/2002 | Wendlandt | G09B 23/285 434/262 |

(Continued)

FOREIGN PATENT DOCUMENTS

| | | |
|---|---|---|
| WO | 2006024033 A3 | 12/2006 |
| WO | 2009137410 A1 | 11/2009 |
| WO | 2010044377 A1 | 4/2010 |

OTHER PUBLICATIONS

Extended European Search Report for EP 19200299.6; dated May 6, 2020; 10 pages.
(Continued)

*Primary Examiner* — Martin T Ton

(57) ABSTRACT

A robotic catheter procedure system is provided. The robotic catheter procedure system includes a bedside system and a remote workstation. The bedside system includes a percutaneous device and a drive mechanism configured to engage and to impart an axial force to the percutaneous device and to advance and retract the percutaneous device. The bedside system includes an actuator providing torque to the drive mechanism to impart the axial force to the percutaneous device, and the torque provided by the actuator is variable. The remote workstation includes a user interface configured to receive a first user input and a control system operatively coupled to the user interface. The control system is configured to communicate a control signal to the actuator. The control signal is based upon the first user input and a second input, and the actuator provides torque to the drive mechanism in response to the control signal.

19 Claims, 13 Drawing Sheets

Related U.S. Application Data continuation of application No. 13/600,816, filed on Aug. 31, 2012, now Pat. No. 9,855,101, which is a continuation of application No. PCT/US2011/026453, filed on Feb. 28, 2011.

(60) Provisional application No. 61/384,174, filed on Sep. 17, 2010, provisional application No. 61/309,774, filed on Mar. 2, 2010.

(51) Int. Cl.
  *A61B 17/00* (2006.01)
  *A61M 25/01* (2006.01)
  *A61B 90/00* (2016.01)

(52) U.S. Cl.
  CPC ... *A61B 2034/301* (2016.02); *A61B 2090/031* (2016.02); *A61B 2090/376* (2016.02); *A61M 25/0113* (2013.01)

(58) Field of Classification Search
  CPC ........ A61B 2090/031; A61B 2090/064; A61B 2090/065; A61B 2090/066; A61B 34/30; A61B 34/37; A61M 2025/0915; A61M 25/0113; A61M 25/0116; A61M 25/09041
  See application file for complete search history.

(56) References Cited

U.S. PATENT DOCUMENTS

| | | | |
|---|---|---|---|
| 6,394,976 | B1 | 5/2002 | Winston et al. |
| 6,726,675 | B1* | 4/2004 | Beyar ............... A61M 25/0113 600/137 |
| 7,819,799 | B2* | 10/2010 | Merril .................. A61B 34/76 606/1 |
| 7,835,630 | B2 | 11/2010 | Kazanzides et al. |
| 2005/0256504 | A1 | 11/2005 | Long et al. |
| 2006/0084945 | A1 | 4/2006 | Moll et al. |
| 2006/0146010 | A1* | 7/2006 | Schneider .......... A61M 25/0113 345/156 |
| 2008/0027313 | A1 | 1/2008 | Shachar |
| 2008/0082109 | A1 | 4/2008 | Moll et al. |
| 2008/0319341 | A1 | 12/2008 | Taylor et al. |
| 2009/0138025 | A1 | 5/2009 | Stahler et al. |
| 2009/0247993 | A1 | 10/2009 | Kirschenman et al. |
| 2010/0057099 | A1* | 3/2010 | Fujimoto ............. G09B 23/285 434/262 |
| 2010/0073150 | A1 | 3/2010 | Olson et al. |

OTHER PUBLICATIONS

International Searching Authority, IPRP including the Written Opinion of the International Searching Authority for Application No. PCT/US2011/026453, dated Sep. 13, 2012, 11 pages.

* cited by examiner

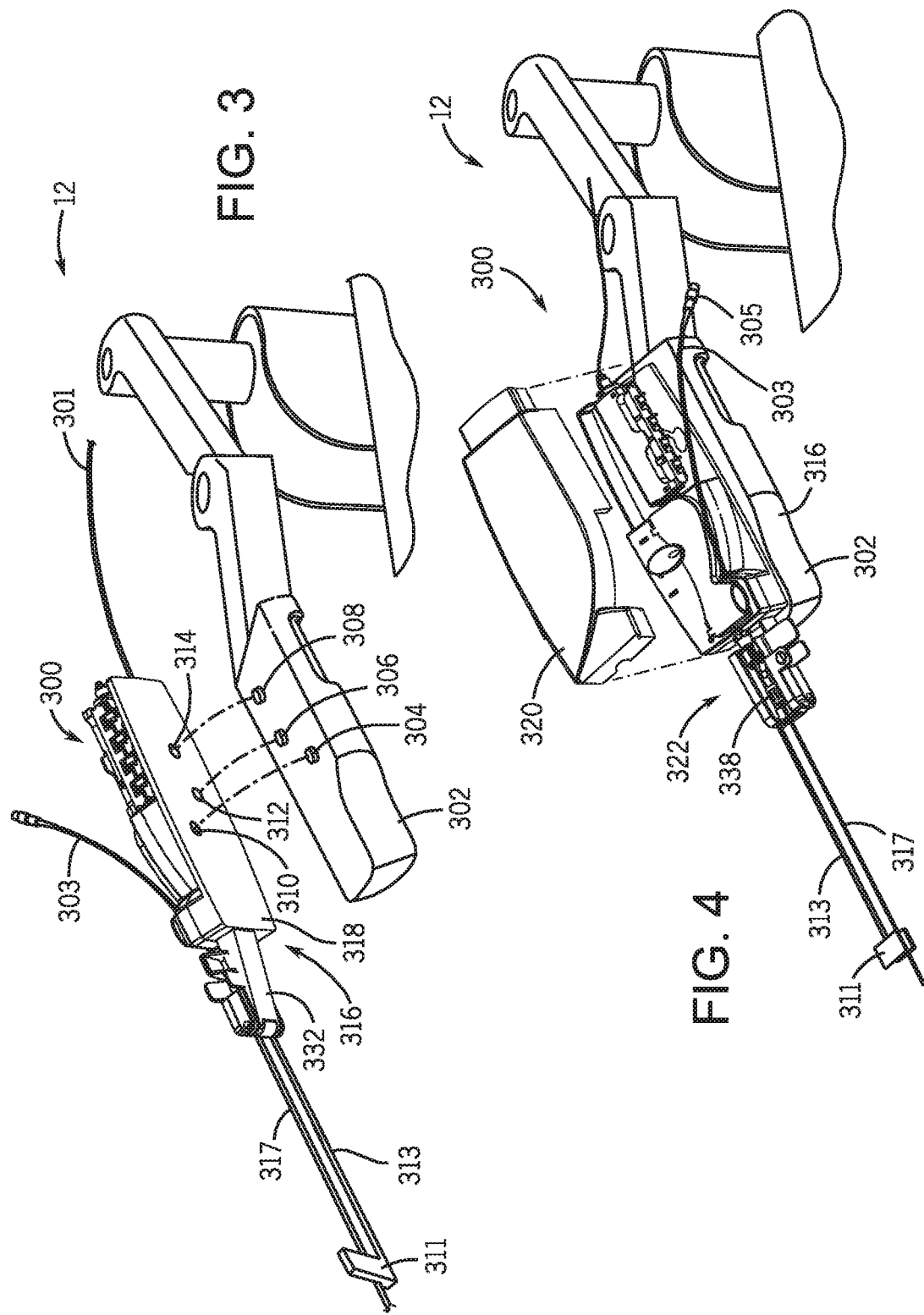

ROBOTIC CATHETER SYSTEM WITH VARIABLE DRIVE MECHANISM

CROSS-REFERENCE TO RELATED PATENT APPLICATION

This application is a continuation of U.S. Non-Provisional application Ser. No. 15/820,753, filed Nov. 22, 2017, entitled ROBOTIC CATHETER SYSTEM WITH VARIABLE DRIVE MECHANISM, which is a continuation of U.S. Non-Provisional application Ser. No. 13/600,816, filed Aug. 31, 2012, entitled ROBOTIC CATHETER SYSTEM WITH VARIABLE DRIVE MECHANISM, now U.S. Pat. No. 9,855,101, which is a continuation Application No. PCT/US2011/026453, filed Feb. 28, 2011, entitled ROBOTIC CATHETER SYSTEM WITH VARIABLE DRIVE MECHANISM, which claims the benefit of U.S. Provisional Application No. 61/309,774, filed Mar. 2, 2010, entitled ROBOTIC CATHETER SYSTEM WITH VARIABLE FORCE DRIVE MECHANISM, and of U.S. Provisional Application No. 61/384,174, filed Sep. 17, 2010, entitled WHEEL FOR ROBOTIC CATHETER SYSTEM DRIVE MECHANISM, all of which are incorporated herein by reference in their entireties.

BACKGROUND OF THE INVENTION

The present invention relates generally to the field of catheter systems for performing diagnostic and/or intervention procedures. The present invention relates specifically to catheter systems configured for controlling and varying the various forces applied to a percutaneous device by a robotic catheter system.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery. If a patient shows symptoms indicative of cardiovascular disease, an image of the patient's heart may be taken to aid in the diagnosis of the patient's disease and to determine an appropriate course of treatment. For certain disease types, such as atherosclerosis, the image of the patient's heart may show a lesion that is blocking one or more coronary arteries. Following the diagnostic procedure, the patient may undergo a catheter based intervention procedure. During one type of intervention procedure, a catheter is inserted into the patient's femoral artery and moved through the patient's arterial system until the catheter reaches the site of the lesion. In some procedures, the catheter is equipped with a balloon or a stent that when deployed at the site of a lesion allows for increased blood flow through the portion of the coronary artery that is affected by the lesion. In addition to cardiovascular disease, other diseases (e.g., hypertension, etc.) may be treated using catheterization procedures.

SUMMARY OF THE INVENTION

One embodiment of the invention relates to a robotic catheter procedure system that includes a bedside system and a remote workstation. The bedside system includes a percutaneous device and a drive mechanism configured to engage and to impart an axial force to the percutaneous device and to advance and retract the percutaneous device. The bedside system includes an actuator providing torque to the drive mechanism to impart the axial force to the percutaneous device, and the torque provided by the actuator is variable. The remote workstation includes a user interface configured to receive a first user input and a control system operatively coupled to the user interface. The control system is configured to communicate a control signal to the actuator. The control signal is based upon the first user input and a second input including information related to the catheter device, and the actuator provides torque to the drive mechanism in response to the control signal. Various exemplary embodiments of the invention relate to the robotic catheter procedure system, as recited above, and including any combination of one or more features as set forth in the claims, recited in the detailed description and shown in the figures.

Another embodiment of the invention relates to a system configured for operating a robotic catheter system having a drive mechanism configured to engage and to impart an axial force to a catheter device and to advance and retract the catheter device and an actuator configured to deliver torque to the drive mechanism. The system includes a user interface configured to receive a first user input and a control system operatively coupled to the user interface configured to generate a control signal. The control signal is based upon the first user input, and the actuator delivers torque to the drive mechanism to move the catheter device in response to the control signal. The system comprises a default maximum torque limit, wherein the actuator is inhibited from delivering torque exceeding the default maximum torque limit. Various exemplary embodiments of the invention relate to a system configured for operating a robotic catheter system, as recited above, and including any combination of one or more features as set forth in the claims, recited in the detailed description and shown in the figures.

Another embodiment of the invention relates to a robotic catheter procedure system including a percutaneous device and a first drive mechanism configured to engage and to impart movement to the percutaneous device. The procedure system also includes an engagement structure. The engagement structure is configured to move between an engaged position in which the engagement structure contacts the percutaneous device and a disengaged position in which the engagement structure does not contact the percutaneous device. The first drive mechanism is configured to move the percutaneous device when the engagement structure is in the disengaged position. Various exemplary embodiments of the invention relate to the robotic catheter procedure system, as recited above, and including any combination of one or more features as set forth in the claims, recited in the detailed description and shown in the figures.

Another embodiment of the invention relates to a method of operating a robotic catheter system. The method includes providing a robotic catheter system. The robotic catheter system includes a percutaneous device, a first drive mechanism having a first engagement structure configured to engage the percutaneous device and to impart movement to the percutaneous device. The catheter procedure system also includes a second engagement structure configured to engage the percutaneous device, and the second engagement structure is moveable between an engaged position in which the second engagement structure contacts the percutaneous device and a disengaged position in which the second engagement structure does not contact the percutaneous device. The method further includes engaging the percutaneous device with both the first engagement structure and the second engagement structure, and disengaging the second engagement structure from the percutaneous device. The method includes operating the first drive mechanism to move the percutaneous device when the second engagement structure is disengaged. Various exemplary embodiments of the invention relate to the method of operating a robotic catheter system, as recited above, and including any combination of one or more features as set forth in the claims, recited in the detailed description and shown in the figures.

Alternative exemplary embodiments relate to other features and combinations of features as may be generally recited in the claims.

BRIEF DESCRIPTION OF THE DRAWINGS

This application will become more fully understood from the following detailed description, taken in conjunction with the accompanying figures, wherein like reference numerals refer to like elements in which:

FIG. 3 is a perspective view of a bedside system showing a cassette prior to being attached to a motor drive base according to an exemplary embodiment;

FIG. 4 is a perspective view of a bedside system showing the cassette of FIG. 3 following attachment to the motor drive base according to an exemplary embodiment;

DETAILED DESCRIPTION OF THE PREFERRED EMBODIMENTS

Before turning to the figures, which illustrate the exemplary embodiments in detail, it should be understood that the present application is not limited to the details or methodology set forth in the description or illustrated in the figures. It should also be understood that the terminology is for the purpose of description only and should not be regarded as limiting.

Figure 1:
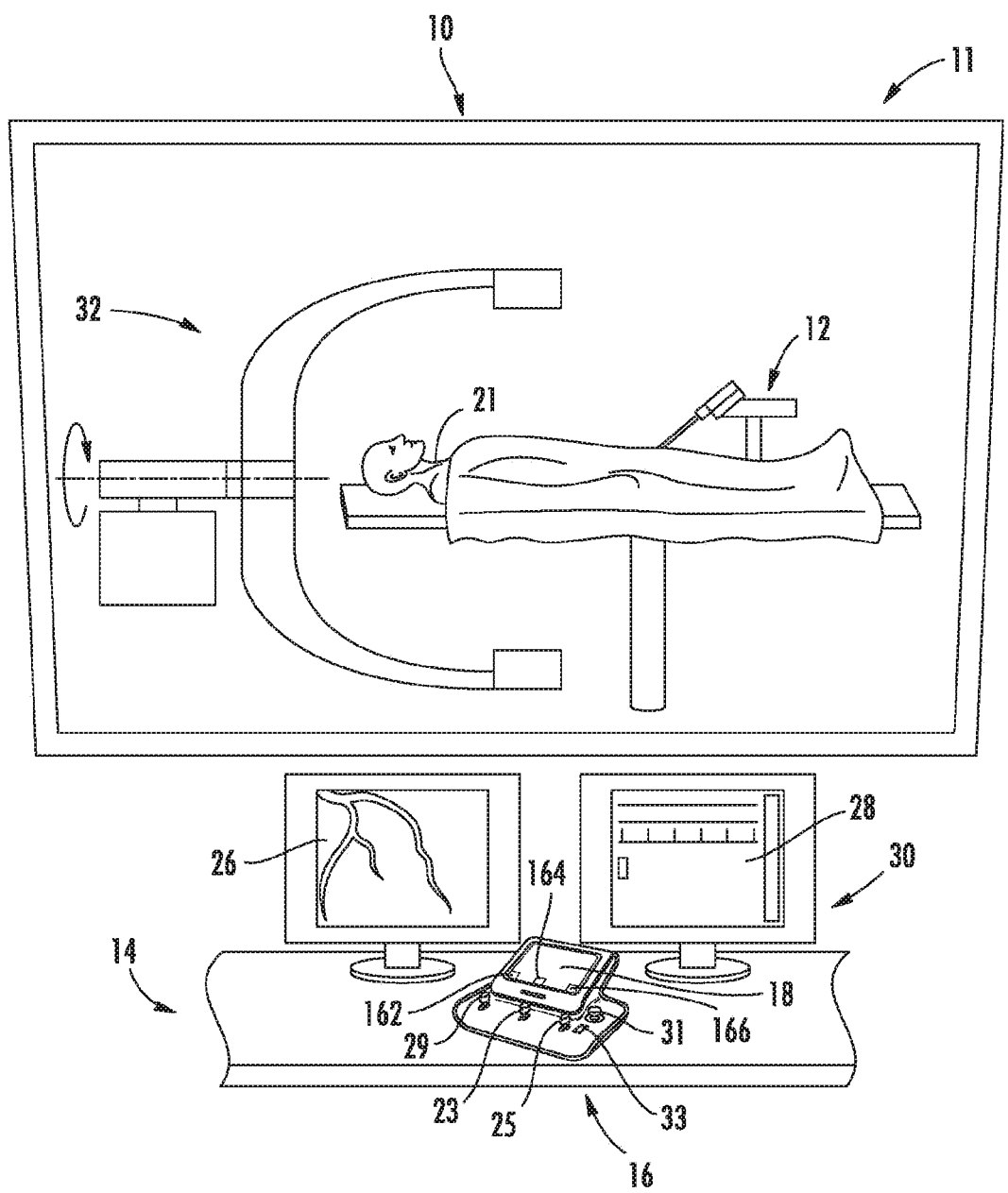
FIG. 1 is a perspective view of a catheter procedure system according to an exemplary embodiment.

Referring to FIG. 1, a catheter procedure system 10 is shown. Catheter procedure system 10 may be used to perform catheter based medical procedures (e.g., percutaneous intervention procedures). Percutaneous intervention procedures may include diagnostic catheterization procedures during which one or more catheters are used to aid in the diagnosis of a patient's disease. For example, during one embodiment of a catheter based diagnostic procedure, a contrast media is injected into one or more coronary arteries through a catheter and an image of the patient's heart is taken. Percutaneous intervention procedures may also include catheter based therapeutic procedures (e.g., balloon angioplasty, stent placement, treatment of peripheral vascular disease, etc.) during which a catheter is used to treat a disease. It should be noted, however, that one skilled in the art would recognize that, certain specific percutaneous intervention devices or components (e.g., type of guide wire, type of catheter, etc.) will be selected based on the type of procedure that is to be performed. Catheter procedure system 10 is capable of performing any number of catheter based medical procedures with minor adjustments to accommodate the specific percutaneous devices to be used in the procedure. In particular, while the embodiments of catheter procedure system 10 described herein are explained primarily in relation to the diagnosis and/or treatment of coronary disease, catheter procedure system 10 may be used to diagnose and/or treat any type of disease or condition amenable to diagnosis and/or treatment via a catheter based procedure.

Catheter procedure system 10 includes lab unit 11 and workstation 14. Catheter procedure system 10 includes a robotic catheter system, shown as bedside system 12, located within lab unit 11 adjacent patient 21. Generally, bedside system 12 may be equipped with the appropriate percutaneous devices (e.g., guide wires, guide catheters, working catheters, catheter balloons, stents, diagnostic catheters, etc.) or other components (e.g., contrast media, medicine, etc.) to allow the user to perform a catheter based medical procedure. A robotic catheter system, such as bedside system 12, may be any system configured to allow a user to perform a catheter-based medical procedure via a robotic system by operating various controls such as the controls located at workstation 14. Bedside system 12 may include any number and/or combination of components to provide bedside system 12 with the functionality described herein. Various embodiments of bedside system 12 are described in detail in P.C.T. International Application No. PCT/US2009/042720, filed May 4, 2009, which is incorporated herein by reference in its entirety.

In one embodiment, bedside system 12 may be equipped to perform a catheter based diagnostic procedure, and in another embodiment, bedside system 12 may be equipped to perform a catheter based therapeutic procedure. Bedside system 12 may be equipped with one or more of a variety of catheters for the delivery of contrast media to the coronary arteries. In one embodiment, bedside system 12 may be equipped with a first catheter shaped to deliver contrast media to the coronary arteries on the left side of the heart, a second catheter shaped to deliver contrast media to the coronary arteries on the right side of the heart, and a third catheter shaped to deliver contrast media into the chambers of the heart. In other embodiments, bedside system 12 may be equipped with a guide catheter, a guide wire, and a working catheter (e.g., a balloon catheter, a stent delivery catheter, ablation catheter, etc.). In one embodiment, bedside system 12 may equipped with a working catheter that includes a secondary lumen that is threaded over the guide wire during a procedure. In another embodiment, bedside system 12 may be equipped with an over-the-wire working catheter that includes a central lumen that is threaded over the guide wire during a procedure. In another embodiment, bedside system 12 may be equipped with an intravascular ultrasound (IVUS) catheter. In another embodiment, any of the percutaneous devices of bedside system 12 may be equipped with positional sensors that indicate the position of the component within the body.

Bedside system 12 is in communication with workstation 14, allowing signals generated by the user inputs and control system of workstation 14 to be transmitted to bedside system 12 to control the various functions of bedside system 12. Bedside system 12 also may provide feedback signals (e.g., operating conditions, warning signals, error codes, etc.) to workstation 14. Bedside system 12 may be connected to workstation 14 via a communication link 38 that may be a wireless connection, cable connectors, or any other means capable of allowing communication to occur between workstation 14 and beside system 12.

Workstation 14 includes a user interface 30. User interface 30 includes controls 16. Controls 16 allow the user to control bedside system 12 to perform a catheter based medical procedure. For example, controls 16 may be configured to cause bedside system 12 to perform various tasks using the various percutaneous devices with which bedside system 12 may be equipped (e.g., to advance, retract, or rotate a guide wire, advance, retract, or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure, etc.).

In one embodiment, controls 16 include a touch screen 18, a dedicated guide catheter control 29, a dedicated guide wire control 23, and a dedicated working catheter control 25. In this embodiment, guide wire control 23 is a joystick configured to cause bedside system 12 to advance, retract, or rotate a guide wire, working catheter control 25 is a joystick configured to cause bedside system 12 to advance, retract, or rotate a working catheter, and guide catheter control 29 is a joystick configured to cause bedside system 12 to advance, retract, or rotate a guide catheter. In addition, touch screen 18 may display one or more icons (such as icons 162, 164, and 166) that control movement of one or more percutaneous devices via bedside system 12. Controls 16 may also include a balloon or stent control that is configured to inflate or deflate a balloon and/or a stent. Each of the controls may include one or more buttons, joysticks, touch screens, etc., that may be desirable to control the particular component to which the control is dedicated.

Controls 16 may include an emergency stop button 31 and a multiplier button 33. When emergency stop button 31 is pushed a relay is triggered to cut the power supply to bedside system 12. Multiplier button 33 acts to increase or decrease the speed at which the associated component is moved in response to a manipulation of guide catheter control 29, guide wire control 23, and working catheter control 25. For example, if operation of guide wire control 23 advances the guide wire at a rate of 1 mm/sec, pushing multiplier button 33 may cause operation of guide wire control 23 to advance the guide wire at a rate of 2 mm/sec. Multiplier button 33 may be a toggle allowing the multiplier effect to be toggled on and off. In another embodiment, multiplier button 33 must be held down by the user to increase the speed of a component during operation of controls 16.

User interface 30 may include a first monitor 26 and a second monitor 28. First monitor 26 and second monitor 28 may be configured to display information or patient specific data to the user located at workstation 14. For example, first monitor 26 and second monitor 28 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 26 and second monitor 28 may be configured to display procedure specific information (e.g., duration of procedure, catheter or guide wire position, volume of medicine or contrast agent delivered, etc.). Monitor 26 and monitor 28 may be configured to display information regarding the position and/or bend of the distal tip of a steerable guide catheter. Further, monitor 26 and monitor 28 may be configured to display information to provide the functionalities associated with the various modules of controller 40 discussed below. In another embodiment, user interface 30 includes a single screen of sufficient size to display one or more of the display components and/or touch screen components discussed herein.

Catheter procedure system 10 also includes an imaging system 32 located within lab unit 11. Imaging system 32 may be any medical imaging system that may be used in conjunction with a catheter based medical procedure (e.g., non-digital x-ray, digital x-ray, CT, MRI, ultrasound, etc.). In an exemplary embodiment, imaging system 32 is a digital x-ray imaging device that is in communication with workstation 14. As shown in FIG. 1, imaging system 32 may include a C-arm that allows imaging system 32 to partially or completely rotate around patient 21 in order to obtain images at different angular positions relative to patient 21 (e.g., sagittal views, caudal views, cranio-caudal views, etc.).

Imaging system 32 is configured to take x-ray images of the appropriate area of patient 21 during a particular procedure. For example, imaging system 32 may be configured to take one or more x-ray images of the heart to diagnose a heart condition. Imaging system 32 may also be configured to take one or more x-ray images during a catheter based medical procedure (e.g., real-time images) to assist the user of workstation 14 to properly position a guide wire, guide catheter, working catheter, stent, etc. during the procedure. The image or images may be displayed on first monitor 26 and/or second monitor 28.

In addition, the user of workstation 14 may be able to control the angular position of imaging system 32 relative to the patient to obtain and display various views of the patient's heart on first monitor 26 and/or second monitor 28. Displaying different views at different portions of the procedure may aid the user of workstation 14 properly move and position the percutaneous devices within the 3D geometry of the patient's heart. In an exemplary embodiment, imaging system 32 may be any 3D imaging modality of the past, present, or future, such as an x-ray based computed tomography (CT) imaging device, a magnetic resonance imaging device, a 3D ultrasound imaging device, etc. In this embodiment, the image of the patient's heart that is displayed during a procedure may be a 3D image. In addition, controls 16 may also be configured to allow the user positioned at workstation 14 to control various functions of imaging system 32 (e.g., image capture, magnification, collimation, c-arm positioning, etc.).

Figure 2:
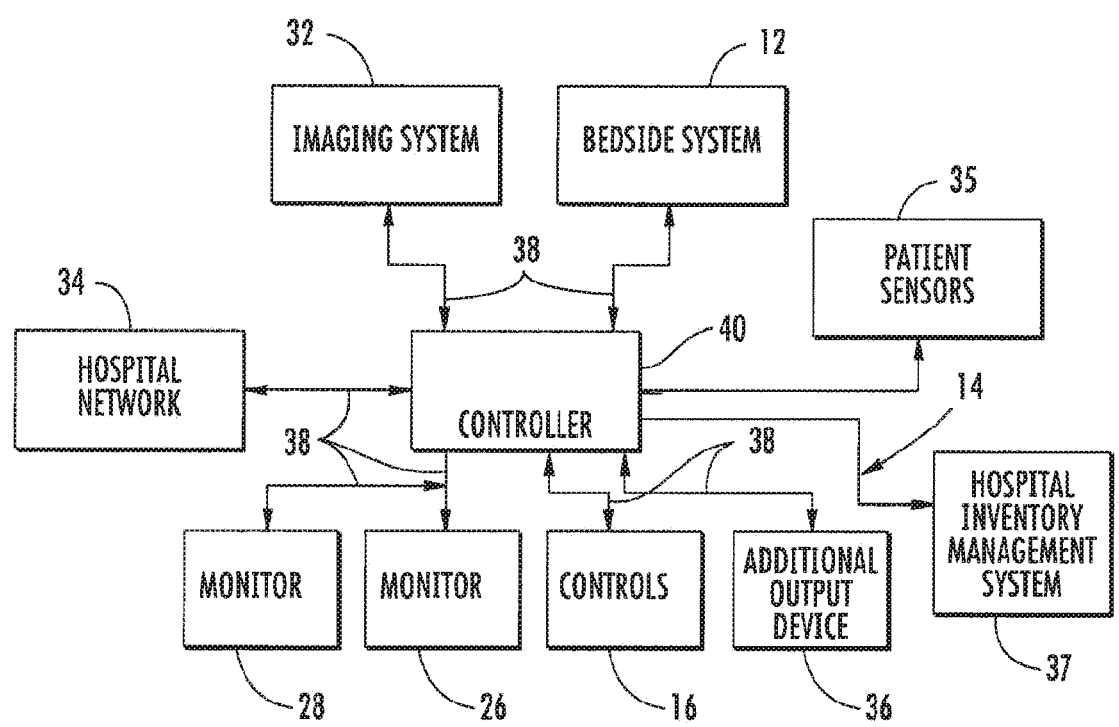
FIG. 2 is a block diagram of a catheter procedure system according to an exemplary embodiment.

Referring to FIG. 2, a block diagram of catheter procedure system 10 is shown according to an exemplary embodiment. Catheter procedure system 10 may include a control system, shown as controller 40. As shown in FIG. 2, controller 40 may be part of workstation 14. Controller 40 is in communication with one or more bedside systems 12, controls 16, monitors 26 and 28, imaging system 32, and patient sensors 35 (e.g., electrocardiogram ("ECG") devices, electroencephalogram ("EEG") devices, blood pressure monitors, temperature monitors, heart rate monitors, respiratory monitors, etc.). In addition, controller 40 may be in communication with a hospital data management system or hospital network 34, one or more additional output devices 36 (e.g., printer, disk drive, cd/dvd writer, etc.), and a hospital inventory management system 37.

Communication between the various components of catheter procedure system 10 may be accomplished via communication links 38. Communication links 38 may be dedicated wires or wireless connections. Communication links 38 may also represent communication over a network. Catheter procedure system 10 may be connected or configured to include any other systems and/or devices not explicitly shown. For example, catheter procedure system 10 may include IVUS systems, image processing engines, data storage and archive systems, automatic balloon and/or stent inflation systems, contrast media and/or medicine injection systems, medicine tracking and/or logging systems, user logs, encryption systems, systems to restrict access or use of catheter procedure system 10, robotic catheter systems of the past, present, or future, etc.

Referring to FIGS. 3-6, an exemplary embodiment of bedside system 12 is shown that is configured to allow a user to advance, retract and rotate a guide wire and to advance and retract a working catheter by operating controls 16 located at workstation 14. In the embodiment shown, bedside system 12 includes a cassette 300 and a motor drive base 302. Cassette 300 is equipped with a guide wire 301 and with a working catheter 303 to allow a user to perform a catheterization procedure utilizing cassette 300. In this embodiment, cassette 300 is configured to be mounted to motor drive base 302. FIG. 3 shows a bottom perspective view of cassette 300 prior to mounting to motor drive base 302. Motor drive base 302 includes a first capstan 304, a second capstan 306, and a third capstan 308. Cassette 300 includes a first capstan socket 310, a second capstan socket 312, and a third capstan socket 314. Cassette 300 includes a housing 316, and housing 316 includes a base plate 318.

Each of the capstan sockets is configured to receive one of the capstans of motor drive base 302. In the embodiment shown, base plate 318 includes a hole or aperture aligned with each of the capstan sockets 310, 312, and 314 to allow each capstan to engage with the appropriate capstan socket. As discussed in more detail below, the engagement between the capstans and capstan sockets allows the transfer of energy (e.g., rotational movement) generated by one or more actuators (e.g., motors) located within motor drive base 302 to each of the drive mechanisms within cassette 300. In one embodiment, a single actuator provides energy to each of the drive mechanisms. In another embodiment, there is an actuator that drives capstan 304, an actuator that drives capstan 306, and an actuator that drives capstan 308. Further, the positioning of the capstans and capstan sockets helps the user to align cassette 300 relative to motor drive base 302 by allowing cassette 300 to be mounted to motor drive base 302 only when all three capstan sockets are aligned with the proper capstan.

In one embodiment, the motors that drive capstans 304, 306, and 308 are located within motor drive base 302. In another embodiment, the motors that drive capstans 304, 306, and 308 may be located outside of base 302 connected to cassette 300 via an appropriate transmission device (e.g., shaft, cable, etc.). In yet another embodiment, cassette 300 includes motors located within the housing of cassette 300. In another embodiment, cassette 300 does not include capstan sockets 310, 312, and 314, but includes an alternative mechanism for transferring energy (e.g., rotational motion) from an actuator external to the cassette to each of the cassette drive mechanisms. For example, rotational movement may be transferred to the drive mechanisms of cassette 300 via alternating or rotating magnets or magnetic fields located within motor drive base 302.

In the embodiment shown, cassette 300 also includes a guide catheter support 311 that supports guide catheter 317 at a position spaced from cassette 300. As shown, guide catheter support 311 is attached to cassette 300 by a rod 313. Rod 313 and guide catheter support 311 are strong enough to support guide catheter 317 without buckling. Guide catheter support 311 supports guide catheter 317 at a position spaced from the cassette, between the patient and the cassette to prevent buckling, bending, etc. of the portion of guide catheter 317 between the cassette and the patient.

Referring to FIG. 4, cassette 300 is shown mounted to motor drive base 302. As shown in FIG. 4, cassette 300 includes an outer cassette cover 320 that may be attached to housing 316. When attached to housing 316, outer cassette cover 320 is positioned over and covers each of the drive mechanisms of cassette 300. By covering the drive assemblies of cassette 300, outer cassette cover 320 acts to prevent accidental contact with the drive mechanisms of cassette 300 while in use.

Figure 5:
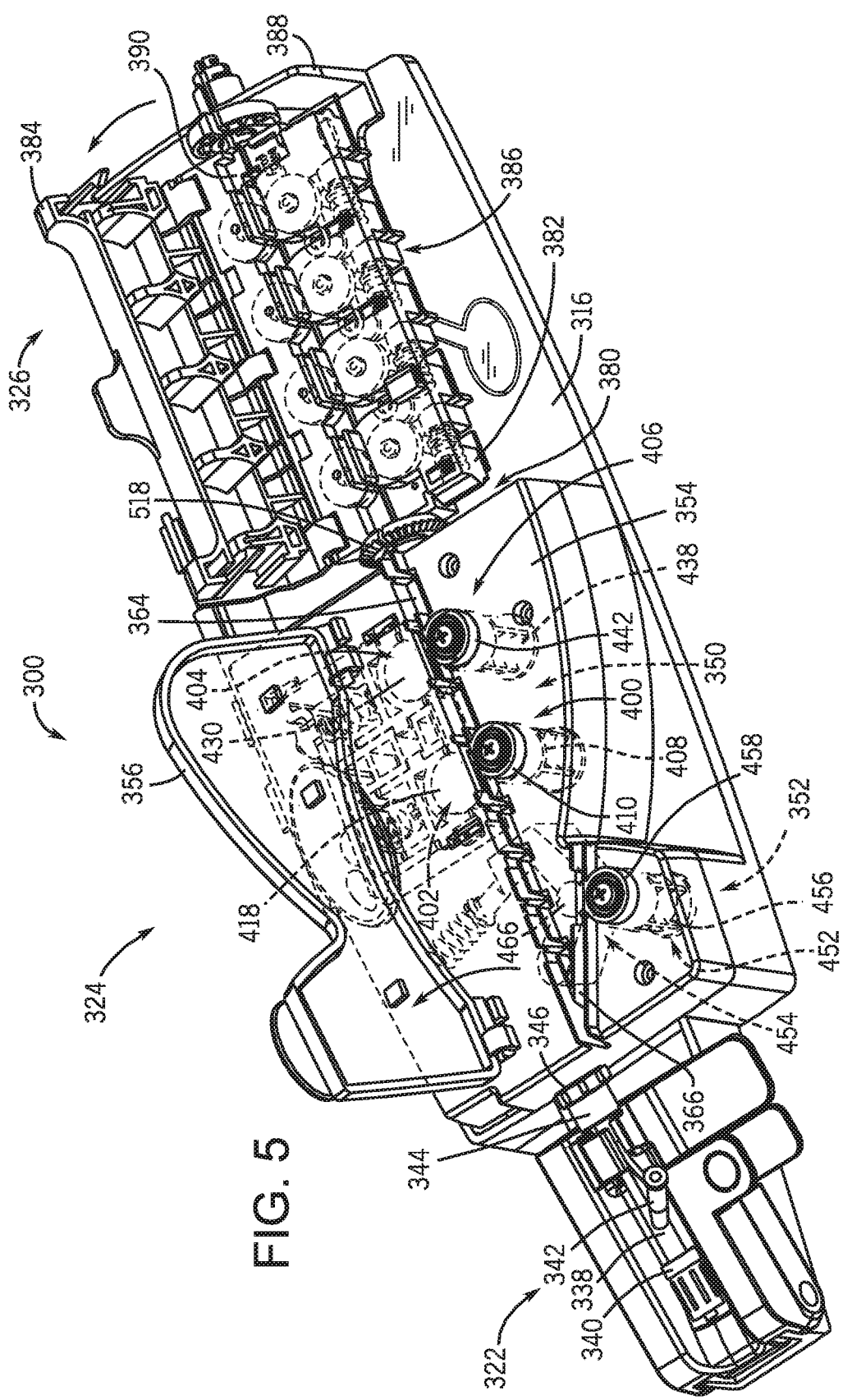
FIG. 5 is a perspective view of a cassette according to an exemplary embodiment.

Referring to FIG. 5, cassette 300 is shown in the "loading" configuration with outer cassette cover 320 removed. Cassette 300 includes a y-connector support assembly 322, an axial drive assembly 324, and a rotational drive assembly 326. Generally, the various portions of cassette 300 are placed in the loading configuration to allow the user to load or install a guide wire and/or working catheter into cassette 300. Cassette 300 includes a Y-connector 338 supported by y-connector support assembly 322. Y-connector 338 includes a first leg 340, a second leg 342, and a third leg 344. First leg 340 is configured to attach to a guide catheter such that the central lumen of the y-connector is in fluid communication with the central lumen of the guide catheter. Second leg 342 is angled away from the longitudinal axis of y-connector 338. Second leg 342 of y-connector 338 allows introduction of a contrast agent or medicine into the lumen of the guide catheter. A one way valve prohibits bodily fluid from exiting second leg 342. Third leg 344 extends away from the guide catheter toward axial drive assembly 324. In use, guide wire 301 and working catheter 303 are inserted into third leg 344 of y-connector 338 via opening 346 and may be advanced through y-connector 338 into the lumen of the guide catheter. The third leg also includes a one way valve that permits insertion and removal of the working catheter and guide wire but prohibits bodily fluids from exiting third leg 344.

Cassette 300 also includes an axial drive assembly 324. Axial drive assembly 324 includes a first axial drive mechanism, shown as guide wire axial drive mechanism 350, and a second axial drive mechanism, shown as working catheter axial drive mechanism 352. Axial drive assembly 324 also includes a top deck 354 and a cover 356.

Generally, in use, a guide wire, such as guide wire 301, is placed within guide wire channel 364 formed in top deck 354, and guide wire axial drive mechanism 350 includes an engagement structure (e.g, a structure including wheels 410 and 418 as discussed below) that is configured to releasably engage and drive (e.g., to impart motion to) guide wire 301 along its longitudinal axis. In this manner, guide wire axial drive mechanism 350 provides for advancement and/or retraction of guide wire 301. In use, a working catheter, such as working catheter 303, is placed within working catheter channel 366 formed in top deck 354, and working catheter axial drive mechanism 352 is configured to releasably engage and drive (e.g., to impart motion to) working catheter 303 along its longitudinal axis. In this manner, working catheter axial drive mechanism 352 provides for advancement and/or retraction of working catheter 303.

Cassette 300 also includes a rotational drive assembly 326. Rotational drive assembly 326 includes a rotational drive mechanism, shown as guide wire rotational drive mechanism 380, a cover 384, and a journal 388. Guide wire rotational drive mechanism 380 includes a chassis 382 and an engagement structure 386. Rotational drive assembly 326 is configured to cause guide wire 301 to rotate about its longitudinal axis. Engagement structure 386 is configured to releasably engage guide wire 301 and to apply sufficient normal force to guide wire 301 such that guide wire 301 is allowed to rotate about its longitudinal axis while permitting guide wire 301 to be moved axially by guide wire axial drive mechanism 350.

As explained in more detail below, in one embodiment, engagement structure 386 includes four pairs of opposed wheels and rotational drive assembly 326 is supported within housing 316 such that rotation drive assembly 326 is permitted to rotate within and relative to housing 316. In use, the guide wire, such as guide wire 301, is received within guide wire channel 390 defined in chassis 382, and the wheels of engagement structure 386 engage guide wire 301 between the wheels of each pair and apply sufficient normal force to guide wire 301 (i.e., the force perpendicular to the outer surface of guide wire 301) such that the rotation of rotational drive assembly 326 causes guide wire 301 to rotate about its longitudinal axis along with rotational drive assembly 326 as rotational drive assembly 326 rotates. Rotational drive mechanism 380 includes a rotation bevel gear 518 that is configured to be coupled to capstan 308 of motor drive base 302 such that rotational drive assembly 326 rotates in response to rotation of capstan 308.

FIG. 5 shows cover 356 and cover 384 in the open positions. When cover 356 and cover 384 are in the open positions, guide wire axial drive mechanism 350, working catheter axial drive mechanism 352, and rotational drive mechanism 380 are exposed allowing the user to load cassette 300 with a guide wire and working catheter. Once the guide wire and working catheter are positioned within guide wire channel 364, guide wire channel 390 and working catheter channel 366, respectively, engagement surfaces of guide wire axial drive mechanism 350, rotational drive mechanism 380 and working catheter axial drive mechanism 352 are brought into engagement with the guide wire and working catheter respectively. With the engagement structures of the respective drive mechanisms engaged, a user may operate controls 16 at workstation 14 to cause movement the guide wire and the working catheter.

Guide wire axial drive mechanism 350 includes a drive element 400, a first roller assembly 402, a second roller assembly 404, and a guide wire axial motion sensor assembly, shown as encoder assembly 406 (first roller assembly 402 and second roller assembly 404 are shown in broken lines in FIG. 5). Drive element 400 includes a drive shaft 408 and a drive wheel 410. Drive shaft 408 is configured to engage second capstan 306 of motor drive base 302 such that drive shaft 408 and drive wheel 410 rotate in response to rotation of second capstan 306. First roller assembly 402 includes an idler wheel or roller 418. Second roller assembly 404 includes an idler wheel or roller 430, and encoder assembly 406 includes shaft 438, idler wheel or roller 442 and a magnetic coupling located at the lower end of shaft 438.

Figure 6:
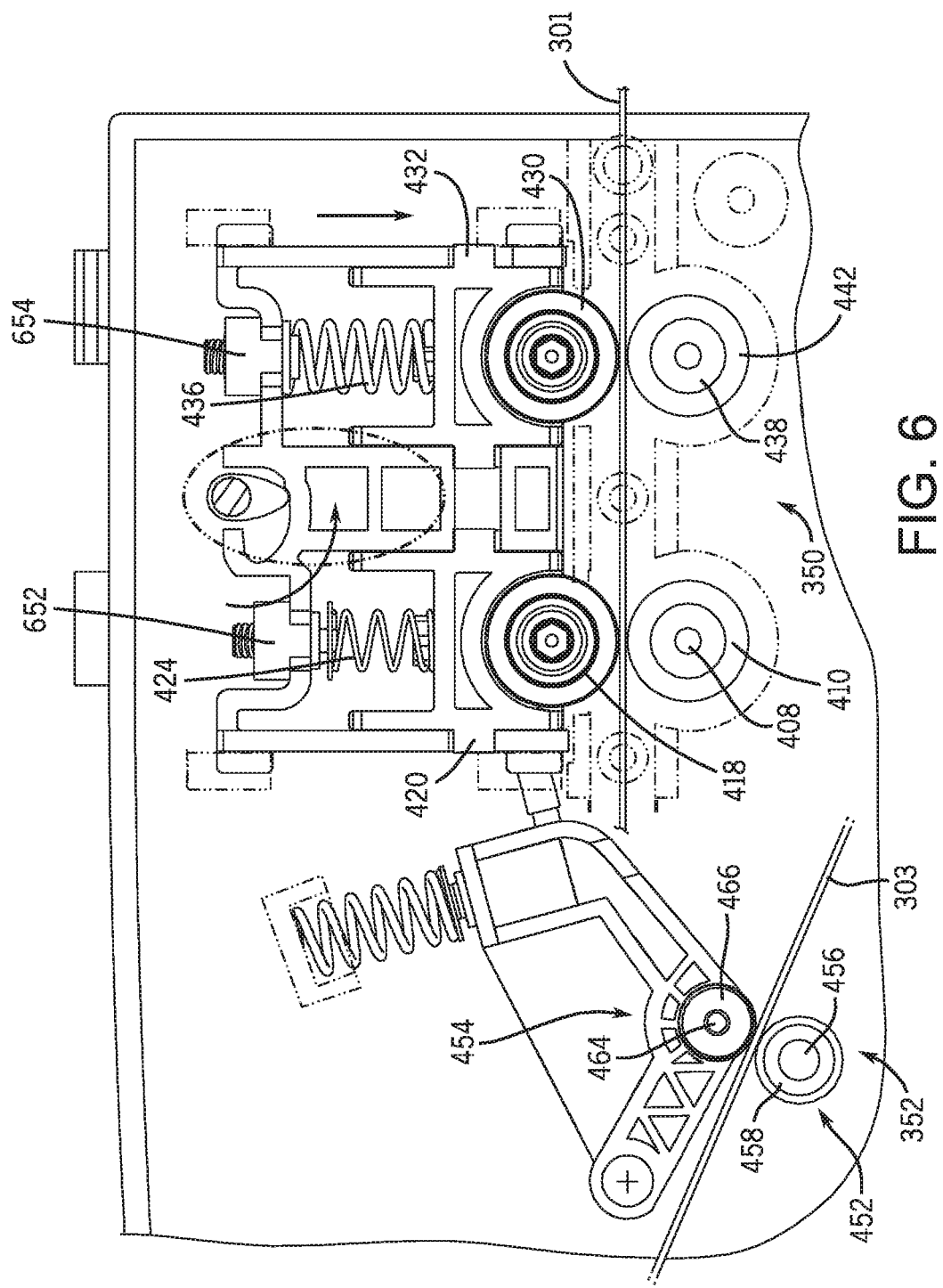
FIG. 6 is a top view showing an axial drive assembly of a cassette in the "engaged" position according to an exemplary embodiment.

Drive wheel 410 includes an outer or engagement surface, and roller 418 includes an outer or engagement surface. Referring to FIG. 6, the "use" or "engaged" position of guide wire axial drive mechanism 350 is shown. Generally, when guide wire axial drive mechanism 350 is placed in the "use" or "engaged" position, guide wire 301 is positioned between drive wheel 410 and roller 418 such that the outer, circumferential surface of drive wheel 410 and the outer, circumferential surface of roller 418 engage the guide wire. In this embodiment, the outer surfaces of drive wheel 410 and roller 418 define a pair of engagement surfaces. The normal force (i.e., the force perpendicular to the surface of guide wire 301) applied to guide wire 301 by drive wheel 410 and roller 418 is such that the friction between drive wheel 410 and guide wire 301 is sufficiently high that drive wheel 410 is able to impart axial motion to guide wire 301 in response to the rotation of drive shaft 408 caused by rotation of second capstan 306. This axial motion allows a user to advance and/or retract a guide wire via manipulation of controls 16 located at workstation 14. Roller 418 is rotatably mounted within wheel housing 420 and rotates freely as drive wheel 410 rotates to drive guide wire 301.

In the "engaged" position shown in FIG. 6, guide wire 301 is positioned between roller 430 and roller 442 such that the outer, circumferential surfaces of roller 430 and of roller 442 engage the guide wire. In this embodiment, the outer surfaces of roller 430 and of roller 442 define a pair of engagement surfaces and form part of an engagement structure of encoder assembly 406. Both rollers 430 and 442 are mounted to rotate freely as drive wheel 410 imparts axial motion to guide wire 301, and the normal force applied to guide wire 301 by the outer surfaces of roller 430 and of roller 442 is such that drive wheel 410 is able to pull guide wire 301 past roller 430 and 442. In this way, the pair of non-active or idle rollers 430 and 442 help support guide wire 301 and maintain alignment of guide wire 301 along the longitudinal axis of cassette 300. Roller 430 is rotatably mounted within wheel housing 432 and roller 442 is rotatably mounted to shaft 438, and both roller 430 and 442 rotate freely as drive wheel 410 moves (e.g., pulls or pushes) guide wire 301 past roller wheels 430 and 442.

Guide wire axial drive mechanism 350 includes a first spring 424 and a second spring 436. Spring 424 is biased to exert a force onto wheel housing 420 causing roller 418 to engage guide wire 301 against drive wheel 410 generating the normal force noted above. Spring 424 is selected such that the proper amount of normal force is applied to guide wire 301 by the engagement surfaces of drive wheel 410 and roller wheel 418 in the "engaged" position. Spring 436 is biased to exert a force onto wheel housing 432 causing roller 430 to engage guide wire 301 against roller 442. Spring 436 is selected such that the proper amount of normal force is applied to guide wire 301 by the engagement surfaces of rollers 430 and 442 in the "engaged" position to support the guide wire while still allowing the guide wire to be moved axially by drive wheel 410. In other embodiments, wheels 418 and 430 may be moved into engagement with guide wire 301 via another mechanism that does not utilize springs 424 and 436. For example, housing 420 and housing 432 may be coupled to a linkage that allows wheels 418 and 430 to be moved to a plurality of positions relative to wheels 410 and 442, and the normal force applied to guide wire 301 is adjusted by varying the distance between wheels 410 and 418 and between wheels 430 and 442 when the wheels engage guide wire 301. In one embodiment, springs 424 and 436 may be tuned and/or adjusted to modify the force applied to guide wire 301 by the wheels of guide wire axial drive mechanism 350.

Because the ability of guide wire axial drive mechanism 350 to move guide 301 may be affected by the friction between the wheels of the drive assembly and guide wire 301, the engagement surfaces of one or more of wheels 410, 418, 430 and 432 may be configured to ensure the proper amount of friction is applied to guide wire 301. In particular, the engagement surface of drive wheel 410 and the engagement surface of roller wheel 418 may be textured (e.g., non-smooth, treaded, slotted, etc.) to increase friction between the wheels and the guide wire. Particular embodiments of a wheel for a robotic catheter system, including a textured engagement surface, are shown and described in detail in U.S. Provisional Application No. 61/384,174, filed Sep. 17, 2010, which is incorporated herein by reference in its entirety.

Thus, the friction or grip between the wheels of guide wire axial drive mechanism 350 and guide wire 301 is a function of the surface properties of the wheels, the surface properties of the guide wire and the normal force exerted between the wheels and the outer surface of the guide wire. The friction between the wheels of guide wire axial drive mechanism 350 and guide wire 301 is a factor in how rotational energy is transferred from drive wheel 410 to guide wire 301 and in how guide wire 301 is moved in response to the transferred energy. As explained in more detail below, by controlling or varying one or more of the properties related to the friction within guide wire axial drive mechanism 350, movement of guide wire 301 can be controlled.

Encoder assembly 406 includes magnetic coupling at the base of shaft 438 that engages a magnetic encoder located within motor drive base 302. The magnetic encoder is configured to measure an aspect (e.g., speed, position, acceleration, etc.) of axial movement of the guide wire. As roller 442 rotates, shaft 438 rotates causing the magnetic coupling to rotate. The rotation of magnetic coupling causes rotation of the magnetic encoder within motor drive base 302. Because rotation of roller 442 is related to the axial movement of guide wire 301, the magnetic encoder within motor drive base 302 is able to provide a measurement of the amount of axial movement experienced by guide wire 301 during a procedure. This information may be used for a variety of purposes. For example, this information may be displayed to a user at workstation 14, may be used in a calculation of or estimated position of the guide wire within the vascular system of a patient, may trigger an alert or alarm indicating a problem with guide wire advancement, etc. Further, as discussed below, this information may be used by procedure control module 98 to calculate and to vary the amount of force or torque being applied to guide wire 301 by drive wheel 410.

Axial drive assembly 324 also includes working catheter axial drive mechanism 352. Working catheter axial drive mechanism 352 includes a drive element 452 and a working catheter axial motion sensor assembly, shown as working catheter encoder assembly 454. Drive element 452 includes a drive shaft 456 and a drive wheel 458. Drive shaft 456 is configured to engage first capstan 304 of motor drive base 302 such that drive shaft 456 and drive wheel 458 rotate in response to rotation of first capstan 304. Encoder assembly 454 includes shaft 464 and a roller 466, and a magnetic coupling located at the lower end of shaft 464.

Drive wheel 458 includes an outer surface and roller 466 includes an outer surface. When working catheter axial drive mechanism 352 is in the "engaged" position, working catheter 303 is positioned between drive wheel 458 and roller 466, such that outer surfaces of drive wheel 458 and roller 466 engage working catheter 303. In this embodiment, the outer surfaces of drive wheel 458 and roller 466 define a pair of engagement surfaces. The force applied to working catheter 303 by the outer surfaces of drive wheel 458 and roller 466 is such that drive wheel 458 is able to impart axial motion to the working catheter in response to the rotation of drive shaft 456 caused by rotation of first capstan 304. This axial motion allows a user to advance and/or retract a working catheter via manipulation of controls 16 located at workstation 14. Roller 466 is rotatably mounted to shaft 464 and rotates freely as drive wheel 458 rotates to drive the working catheter.

Encoder assembly 454 includes a magnetic coupling located at the lower end of shaft 464 that engages a magnetic encoder located within motor drive base 302. The magnetic encoder is configured to measure an aspect (e.g., speed, position, acceleration, etc.) of axial movement of the working catheter. As roller 466 rotates, shaft 464 rotates causing the magnetic coupling to rotate. The rotation of the magnetic coupling causes rotation of the magnetic encoder within motor drive base 302. Because rotation of roller 466 is related to the axial movement of working catheter 303, the magnetic encoder within motor drive base 302 is able to provide a measurement of the amount of axial movement experienced by the working catheter during a procedure. This information may be used for a variety of purposes. For example, this information may be displayed to a user at workstation 14, may be used in a calculation of or estimated position of the working catheter within the vascular system of a patient, may trigger an alert or alarm indicating a problem with working catheter advancement, etc. Further, as discussed below in relation to the guide wire motor, this information may be used by procedure control module 98 to calculate and to vary the amount of force or torque being applied to working catheter 303 by drive wheel 458.

Figure 7:
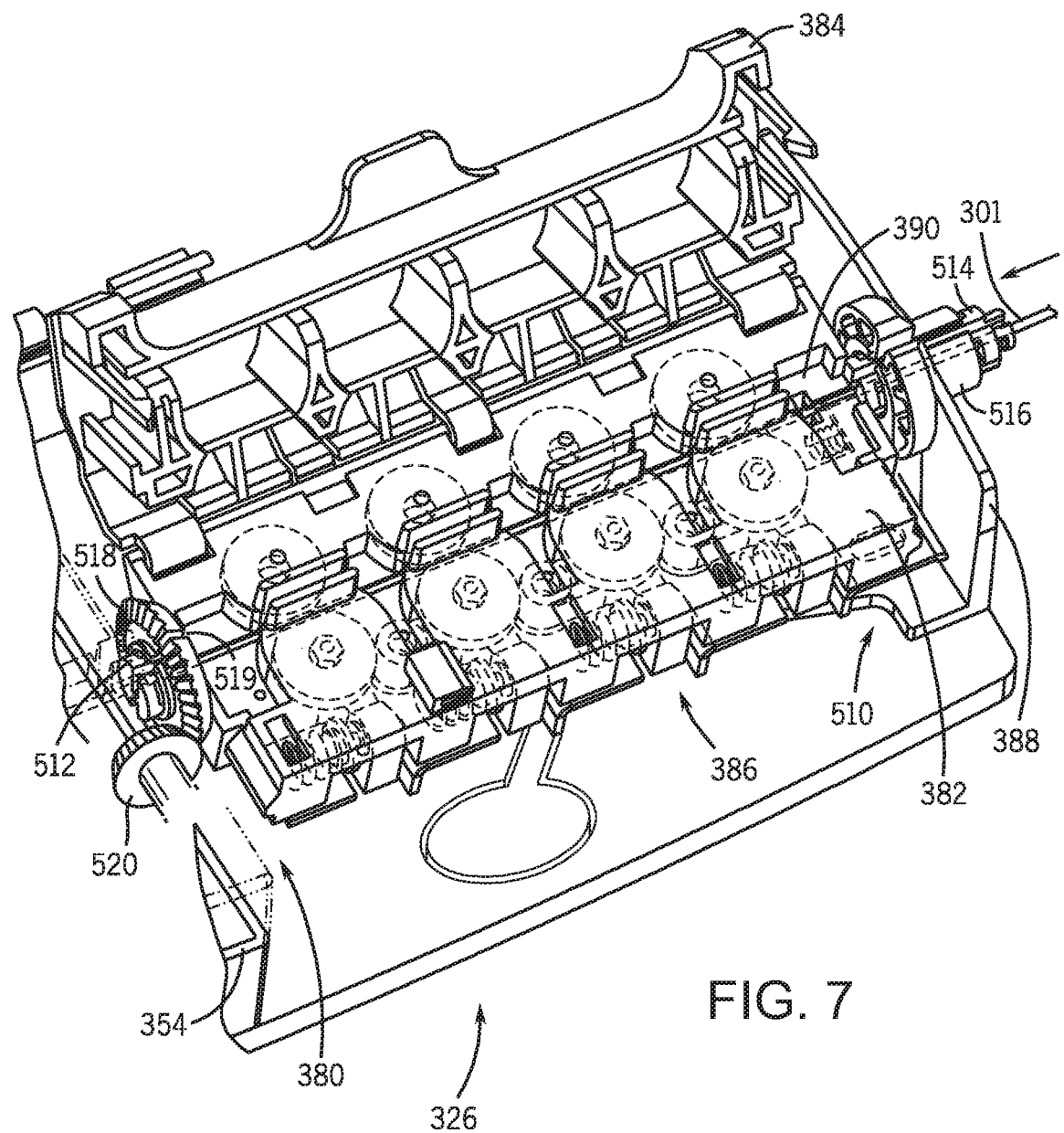
FIG. 7 is a top perspective view of a rotational drive assembly of a cassette showing the engagement structure in broken lines beneath the chassis.
Figure 8:
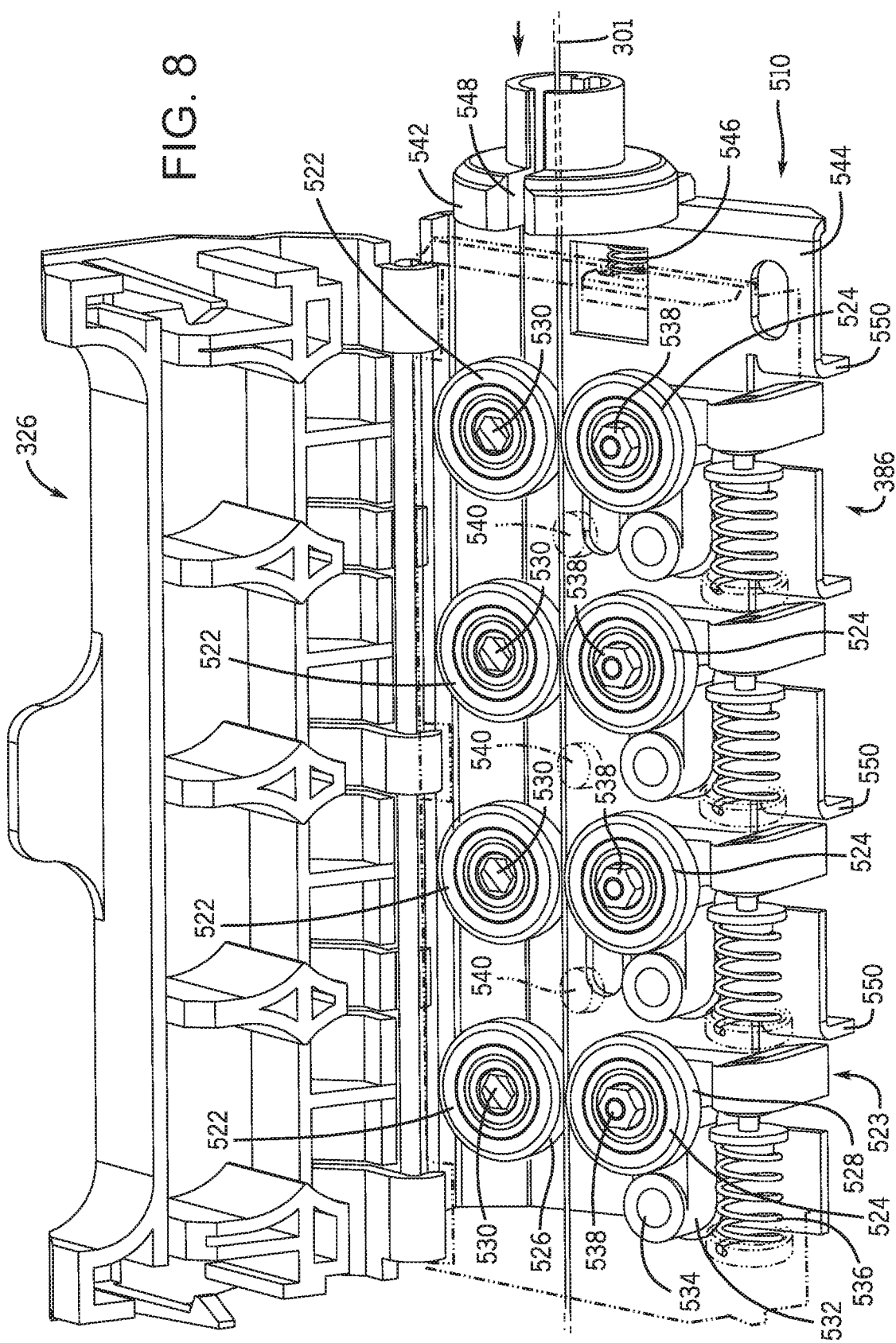
FIG. 8 is a top perspective view of a rotational drive assembly with the chassis shown in broken lines.

FIGS. 7 and 8 show perspective views of rotational drive assembly 326 showing cover 384 in the open position. Rotational drive assembly 326 includes rotational drive mechanism 380, chassis 382, an engagement structure 386, and a disengagement assembly 510. Chassis 382 fits over engagement structure 386 and provides mounting for various components of rotational drive assembly 326. Chassis 382 includes a front shaft 512 and a rear shaft 514. Front shaft 512 is rotatably received within a collar (shown in broken lines) of top deck 354, and rear shaft 514 is rotatably received within collar 516 such that rotational drive mechanism 380 is able to rotate relative to journal 388. As shown, collar 516 extends through and is supported by journal 388 such that rear shaft 514 rotates within collar 516 as rotational drive mechanism 380 is rotated. Collar 516 rests within a recess or slot formed within journal 388. In another embodiment, rear shaft 514 may be in direct contact with journal 388 such that rear shaft 514 rotates within the recess or slot of journal 388 as rotational drive mechanism 380 is rotated.

Guide wire channel 390 extends the length of chassis 382 through both front shaft 512 and rear shaft 514.

Rotational drive mechanism 380 includes rotation bevel gear 518 that engages a drive gear 520. Bevel gear 518 is rigidly coupled to front shaft 512 of chassis 382 such that rotation of bevel gear 518 rotates chassis 382. Drive gear 520 is coupled to a rotational actuator positioned in motor drive base 302 and engages bevel gear 518. Rotation of the rotational actuator in motor drive base 302 causes drive gear 520 to rotate which causes bevel gear 518 to rotate which in turn causes rotational drive mechanism 380 to rotate. Rotational drive mechanism 380 is allowed to rotate about the longitudinal axis of guide wire channel 390 via the rotatable connections between front shaft 512 and top deck 354 and between rear shaft 514 and journal 388. Bevel gear 518 further includes a slot 519 in axial alignment with guide wire channel 390. Slot 519 allows the user to place guide wire 301 into guide wire channel 390 by dropping it in vertically as opposed to threading it through bevel gear 518. In one embodiment, rotational drive assembly 326 is equipped with one or more sensors that are configured to measure an aspect (e.g., speed, position, acceleration, etc.) of rotation of the guide wire and/or any other structure of rotational drive assembly 326. The sensors that measure rotation of the guide wire may include magnetic encoders and/or optical sensors as discussed above regarding the sensors that measure axial motion of the guide wire and/or working catheter. However, any suitable sensor (e.g., resolvers, sychros, potentiometers, etc.) may be used to detect rotation of the guide wire.

Referring to FIG. 8, engagement structure 386 is shown according to an exemplary embodiment. As shown, engagement structure 386 includes four pairs of idler wheels or rollers. Each pair of rollers includes a fixed wheel 522 and an engagement wheel 524. Fixed wheels 522 are rotatably coupled to chassis 382 via fixation posts 530. Each engagement wheel 524 is part of an engagement wheel assembly 523. Each engagement wheel assembly 523 includes a pivot yoke 532 and a spring 536. Each engagement wheel is mounted to pivot yoke 532 via a mounting post 538. Each pivot yoke 532 is pivotally coupled to chassis 382 via fixation posts 534.

Figure 9:
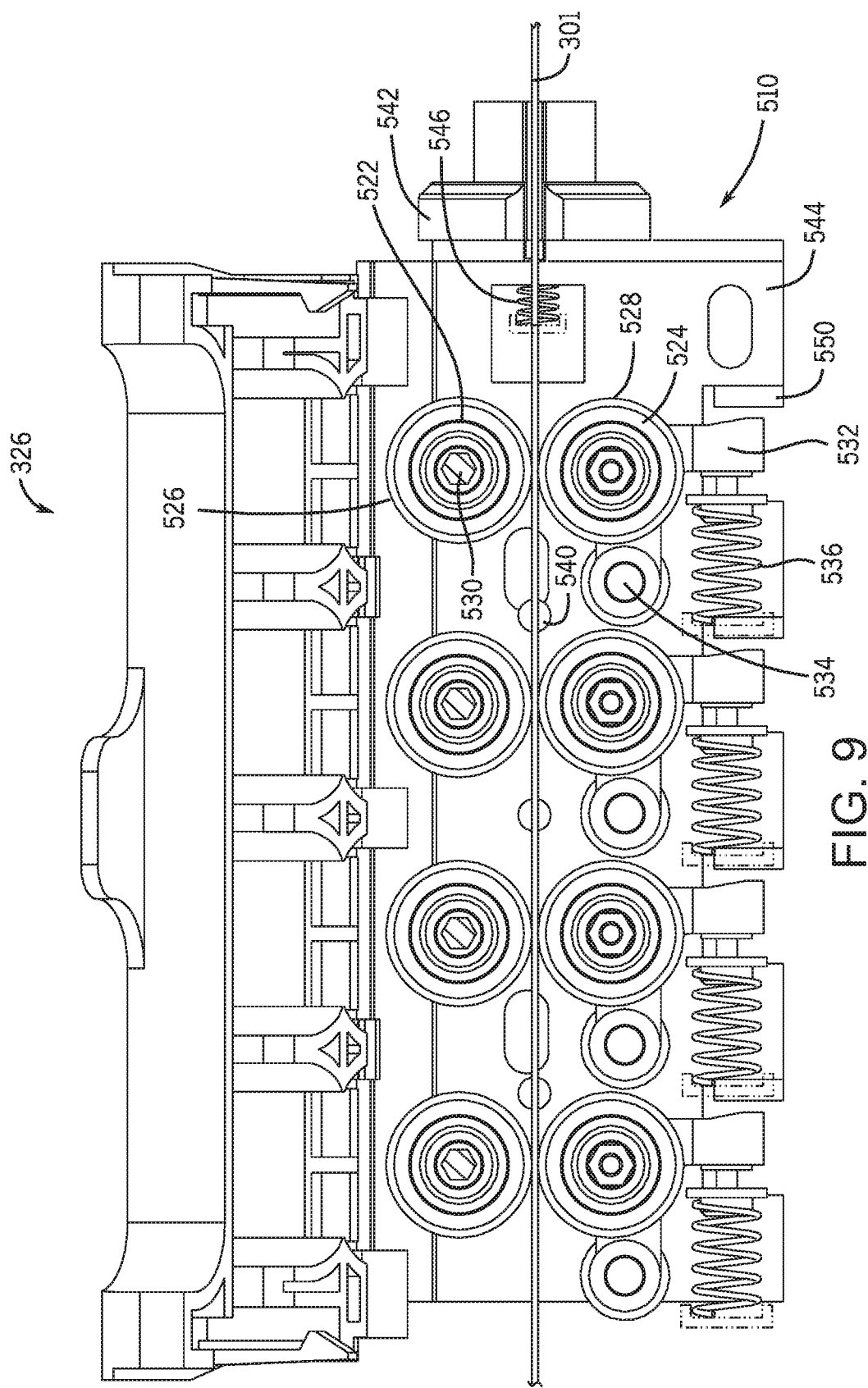
FIG. 9 is a top view of the rotational drive assembly in the "engaged" position.

Each fixed wheel 522 includes an outer or engagement surface 526 and each engagement wheel 524 includes an outer or engagement surface 528. Generally, FIG. 8 and FIG. 9 show engagement structure 386 in the "use" or "engaged" position. In the "engaged" position, guide wire 301 is positioned between fixed wheels 522 and engagement wheels 524 such that engagement surfaces 526 and 528 are able to engage guide wire 301. In this embodiment, engagement surface 526 and engagement surface 528 of each pair of rollers define a pair of engagement surfaces. The normal force applied to guide wire 301 by engagement surfaces 526 and 528 is sufficient to cause the guide wire to rotate about its longitudinal axis as rotational drive assembly 326 is rotated within the housing of cassette 300. Further, the force applied to guide wire 301 by engagement surfaces 526 and 528 is also sufficient to allow the guide wire to be moved axially by guide wire axial drive mechanism 350.

Springs 536 are biased to exert a force onto pivot yokes 532 causing each engagement wheel 524 to engage the opposite fixed wheel 522. The generally L-shape of pivot yoke 532 allows springs 536 to be aligned with the longitudinal axis of guide wire 301 and still cause engagement between engagement wheels 524, fixed wheels 522, and the guide wire. This allows the lateral dimension of rotational drive assembly 326 to be less than if springs 536 were positioned perpendicular to the longitudinal axis of the guide wire. Springs 536 are selected, tuned, and/or adjusted such that the proper amount of normal force is applied to the guide wire by engagement surfaces 526 and 528 in the "engaged" position.

Cassette 300 also includes a series of magnets 540 located beneath guide wire channel 390. Because, in at least some embodiments the guide wire is made from a magnetic material, magnets 540 are able to interact with the guide wire. In this embodiment, the magnetic attraction created by magnets 540 helps the user position guide wire 301 during loading by drawing guide wire 301 into guide wire channel 390. The magnetic attraction created by magnets 540 also tends to hold guide wire 301 within guide wire channel 390 during advancement and/or retraction of the guide wire. Further, magnets 540 help to hold guide wire 301 straight (i.e., parallel to the longitudinal axis of guide wire channel 390) to aid in the axial movement caused by guide wire axial drive mechanism 350.

Rotational drive assembly also includes a disengagement assembly 510. Disengagement assembly 510 includes a stepped collar 542, a base plate 544, and a spring 546. Stepped collar 542 is coupled to base plate 544, and spring 546 is coupled at one end to chassis 382 and at the other end to base plate 544. Stepped collar 542 includes a slot 548 in axial alignment with guide wire channel 390. Like slot 519, slot 548 allows the user to place guide wire 301 into guide wire channel 390 by dropping it in vertically as opposed to threading it through stepped collar 542. Base plate 544 includes a plurality of engagement arms 550 that extend generally perpendicular to the plane defined by base plate 544.

Figure 10:
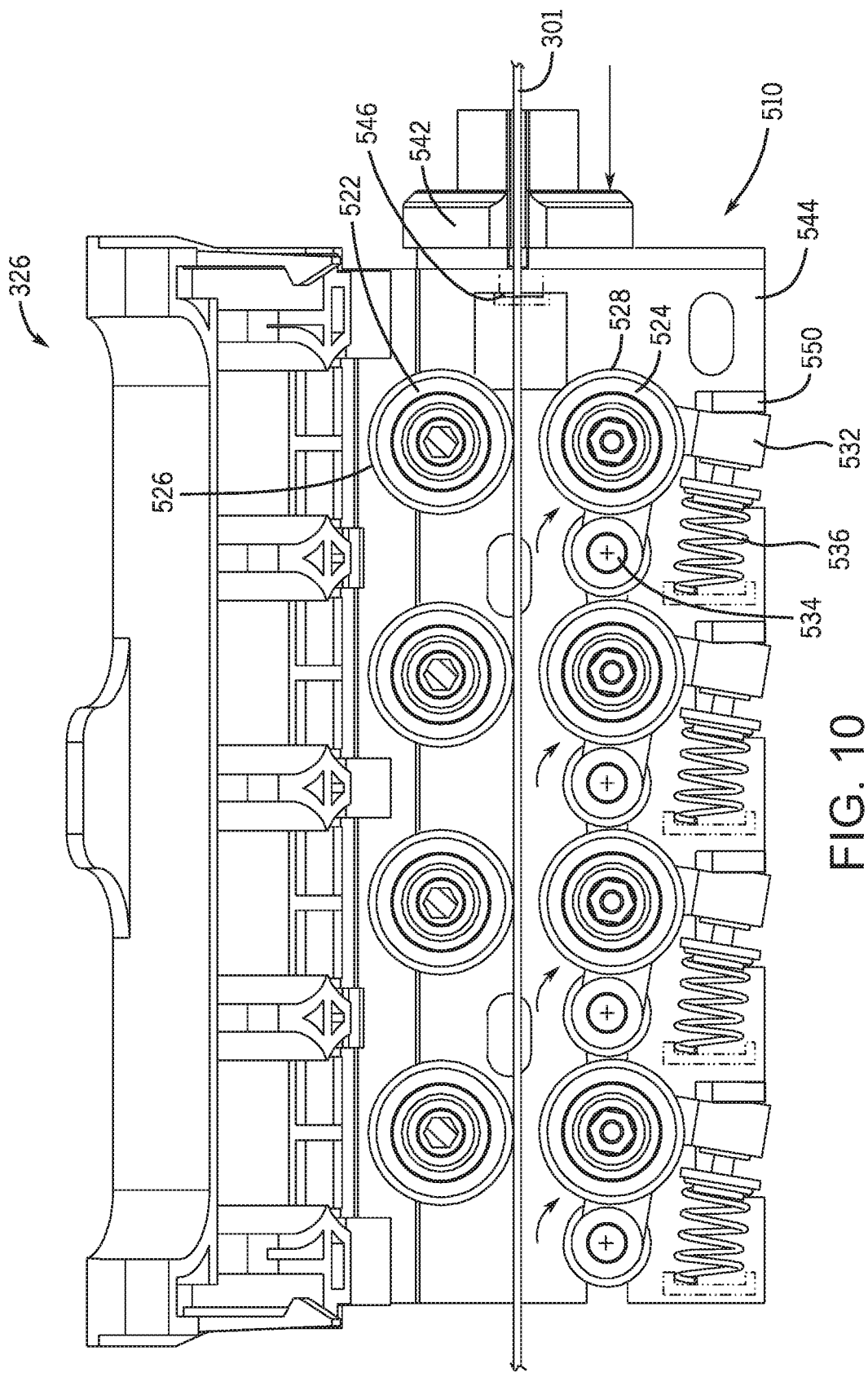
FIG. 10 is a top view of the rotational drive assembly in the "disengaged" position.

Generally, disengagement assembly 510 allows engagement wheels 524 to be moved away from fixed wheels 522. Referring to FIGS. 9 and 10, FIG. 10 shows a top view of rotational drive assembly 326 in the disengaged configuration, and FIG. 9 shows a top view of rotational drive assembly 326 in the engaged configuration. To cause engagement wheels 524 to disengage from guide wire 301, an axially directed force (depicted by the arrow in FIG. 10) is applied to stepped collar 542. This causes base plate 544 to move toward the front of cassette 300 in the direction of the arrow. As base plate 544 moves forward, spring 546 is compressed, and engagement arms 550 are brought into contact with pivot yokes 532. The contact between engagement arms 550 and pivot yokes 532 causes springs 536 to be compressed, and pivot yokes 532 pivot about fixation posts 534. As pivot yokes 532 pivot, engagement wheels 524 are drawn away from fixed wheels 522 such that engagement wheels 524 and fixed wheels 522 are not in contact with guide wire 301. As shown in FIG. 10, this provides sufficient space between engagement wheels 524 and fixed wheels 522 to allow the user to place guide wire 301 into guide wire channel 390, and, as explained below, also allows for the reduction of friction or drag that is exerted on the guide wire by rotational drive mechanism 380 during axial movement.

When the axial force is removed from stepped collar 542, engagement wheels 524 move from the position shown in FIG. 10 to the "engaged" position shown in FIG. 9. When the axial force is removed, spring 546 and springs 536 are allowed to expand causing engagement arms 550 to disengage from pivot yokes 532. Pivot yokes 532 pivot counterclockwise about fixation posts 534, bringing engagement wheels 524 back toward guide wire channel 390 causing engagement surfaces 526 of fixed wheels 522 and engagement surfaces 528 of engagement wheels 524 to engage guide wire 301.

In one embodiment, a user may activate controls located at workstation 14 to cause rotational drive assembly 326 to move between the engaged position of FIG. 9 and the disengaged position of FIG. 10. In one embodiment, rotational drive assembly may be placed in the disengaged position of FIG. 10 in response to the user input to facilitate loading and unloading of the guide wire. In one such embodiment, rotational drive assembly 326 is automatically rotated such that guide wire channel 390 is facing generally upward to allow for easy loading or removal of the guide wire. In the embodiment shown, chassis 382 rotates relative to stepped collar 542. In this embodiment, when rotational drive assembly 326 is in the "loading" position, a path defined by the engagement surfaces of engagement structure 386 and guide wire channel 390 align with slot 548 of stepped collar 542. With guide wire channel 390 facing upward, cover 384 is moved from the closed position to the open position allowing the user to access guide wire channel 390 to either remove or install the guide wire.

Motor drive base 302 may include a structure (e.g., structure 610 shown in FIG. 12 and discussed in more detail below) that applies the axial force to stepped collar 542 in response to a user's activation of controls located at workstation 14. The structure applies the axial force to the stepped collar 542 to cause engagement structure 386 to disengage from the guide wire as discussed above. In one embodiment, cassette 300 and/or motor drive base 302 may also include one or more motors or other actuators that cause the covers of cassette 300 to open in response to a user's activation of controls at workstation 14.

Figure 11:
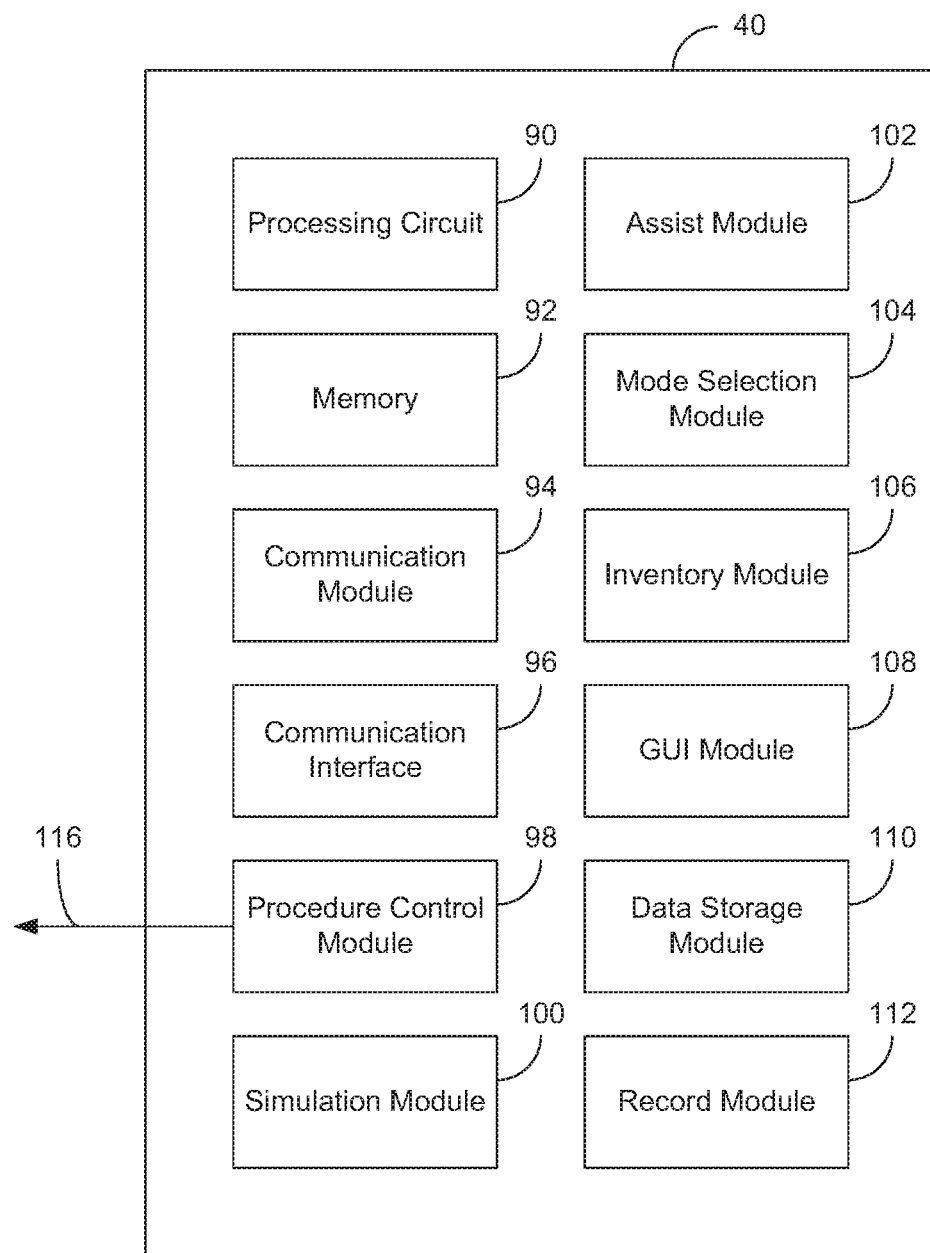
FIG. 11 is a block diagram of a controller for controlling a robotic catheter system according to an exemplary embodiment.

Referring to FIG. 11, a block diagram of controller 40 is shown according to an exemplary embodiment. Controller 40 may generally be an electronic control unit suitable to provide catheter procedure system 10 with the various functionalities described herein. For example, controller 40 may be an embedded system, a dedicated circuit, a general purpose system programmed with the functionality described herein, etc. Controller 40 includes a processing circuit 90, memory 92, communication module or subsystem 94, communication interface 96, procedure control module or subsystem 98, simulation module or subsystem 100, assist control module or subsystem 102, mode selection module or subsystem 104, inventory module or subsystem 106, GUI module or subsystem 108, data storage module or subsystem 110, and record module or subsystem 112.

Processing circuit 90 may be a general purpose processor, an application specific processor (ASIC), a circuit containing one or more processing components, a group of distributed processing components, a group of distributed computers configured for processing, etc., configured provide the functionality of module or subsystem components 94, 98-112. Memory 92 (e.g., memory unit, memory device, storage device, etc.) may be one or more devices for storing data and/or computer code for completing and/or facilitating the various processes described in the present disclosure. Memory 92 may include volatile memory and/or non-volatile memory. Memory 92 may include database components, object code components, script components, and/or any other type of information structure for supporting the various activities described in the present disclosure.

According to an exemplary embodiment, any distributed and/or local memory device of the past, present, or future may be utilized with the systems and methods of this disclosure. According to an exemplary embodiment, memory 92 is communicably connected to processing circuit 90 and module components 94, 98-112 (e.g., via a circuit or any other wired, wireless, or network connection) and includes computer code for executing one or more processes described herein. A single memory unit may include a variety of individual memory devices, chips, disks, and/or other storage structures or systems.

Module or subsystem components 94, 98-112 may be computer code (e.g., transitory program instructions, non-transitory program instructions, object code, program code, compiled code, script code, executable code, or any combination thereof), hardware, software, or any combination thereof, for conducting each module's respective functions. Module components 94, 98-112 may be stored in memory 92, or in one or more local, distributed, and/or remote memory units configured to be in communication with processing circuit 90 or another suitable processing system.

Communication interface 96 includes one or more component for communicably coupling controller 40 to the other components of catheter procedure system 10 via communication links 38. Communication interface 96 may include one or more jacks or other hardware for physically coupling communication links 38 to controller 40, an analog to digital converter, a digital to analog converter, signal processing circuitry, and/or other suitable components. Communication interface 96 may include hardware configured to connect controller 40 with the other components of catheter procedure system 10 via wireless connections. Communication module 94 is configured to support the communication activities of controller 40 (e.g., negotiating connections, communication via standard or proprietary protocols, etc.).

Data storage module 110 is configured to support the storage and retrieval of information by controller 40. In one embodiment, data storage module 110 is a database for storing patient specific data, including image data. In another embodiment, data storage module 110 may be located on hospital network 34. Data storage module 110 and/or communication module 94 may also be configured to import and/or export patient specific data from hospital network 34 for use by controller 40.

Controller 40 also includes simulation module or subsystem 100, assist module or subsystem 102, mode selection module or subsystem 104, inventory module or subsystem 106, GUI module or subsystem 108, data storage module or subsystem 110, and record module or subsystem 112. Generally, simulation module 100 is configured to run a simulated catheterization procedure based upon stored vascular image data and also based upon a user's manipulation of controls 16. Generally, assist module 102 is configured to provide information to the user located at workstation 14 during a real and/or simulated catheterization procedure to assist the user with the performance of the procedure. Specific embodiments of controller 40, including specific embodiments of simulation module 100, and assist module 102, are described in detail in P.C.T. International Application No. PCT/US2009/055318, filed Aug. 28, 2009, which is incorporated herein by reference in its entirety. Other specific embodiments of controller 40, including specific embodiments of GUI module 108, are described in P.C.T. International Application No. PCT/US2009/055320, filed Aug. 28, 2009, which is incorporated herein by reference in its entirety.

Figure 12:
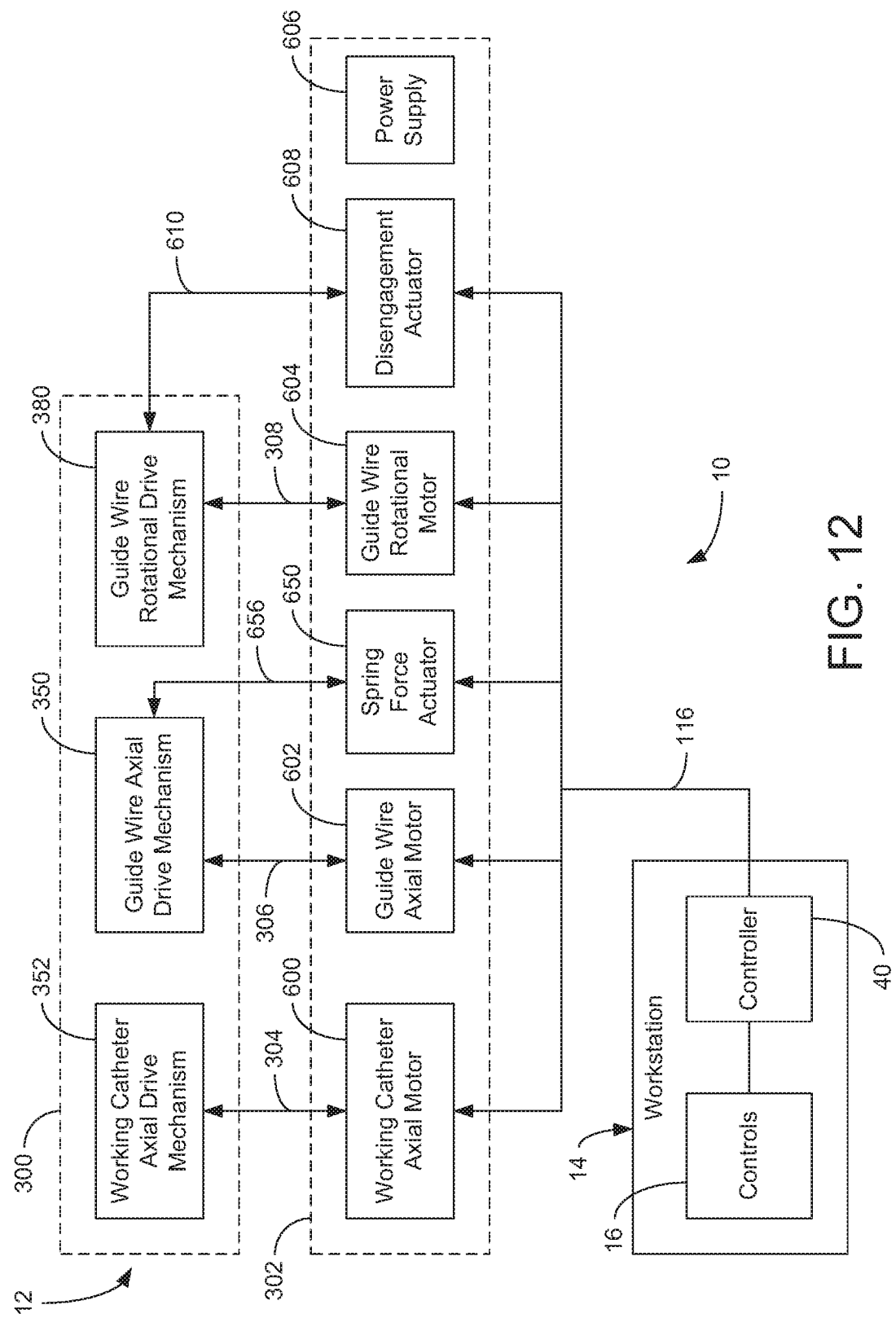
FIG. 12 is a block diagram of a catheter procedure system showing motors located within a motor drive base according to an exemplary embodiment.

Controller 40 also includes a procedure control module 98 configured to support the control of bedside system 12 during a catheter based medical procedure. Procedure control module 98 allows the user to operate bedside system 12 by manipulating controls 16. In various embodiments, procedure control module 98 is configured to generate one or more control signals 116 based upon a first user input (e.g., the user's manipulation of controls 16) and, in some embodiments, also based upon a second input such as various data and information available to procedure control module 98. In various embodiments discussed in more detail below, the second input includes information related to the catheter device. As shown in FIG. 12, control signals 116 generated by procedure control module 98 are communicated from controller 40 to the actuators or motors of bedside system 12. In response to control signals 116, the motors of bedside system 12 drive the drive mechanisms of cassette 300 (e.g., guide wire axial drive mechanism 350, working catheter axial drive mechanism 352, guide wire rotational drive mechanism 380, etc.) to cause movement of the guide wire or working catheter in accordance with the manipulation of controls 16 by the user. Procedure control module 98 may also cause data appropriate for a particular procedure to be displayed on monitors 26 and 28. Procedure control module 98 may also cause various icons (e.g., icons 162, 164, 166, etc.) to be displayed on touch screen 18 that the user may interact with to control the use of bedside system 12.

Referring to FIG. 12, a block diagram of catheter procedure system 10 is shown according to an exemplary embodiment. In the exemplary embodiment of FIG. 12, motor drive base 302 includes working catheter axial drive motor 600, guide wire axial drive motor 602, a guide wire rotational drive motor 604, a power supply 606, and a disengagement actuator 608. Working catheter axial drive motor 600 drives capstan 304, guide wire axial drive motor 602 drives capstan 306 and guide wire rotational drive motor 604 drives capstan 308 to cause movement of working catheter 303 and guide wire 301, as discussed above. Motors 600, 602 and 604 are in communication with controller 40 such that control signals 116 may be received by motors 600, 602 and 604. Motors 600, 602 and 604 respond to control signals 116 by varying the rotation of capstans 304, 306 and 308 thereby varying the movement of working catheter 303 and guide wire 301 caused by drive mechanisms 352, 350 and 380. As shown, motor drive base 302 also includes a power supply 606 that may be, for example, a battery, the AC building power supply, etc.

Movement of a percutaneous device using a robotic system may be affected by a number of interrelated factors. For example, movement of a percutaneous device may be effected by the friction between the percutaneous device and the portions of the engagement structure imparting movement to the device (e.g., drive wheel 410) and also on the friction between the percutaneous device and non-active or supporting portions of the engagement structure (e.g., roller wheels 418, 430 and 442). Movement of a percutaneous device may be effected by on the friction or drag applied to the percutaneous device by other structures within the system, and it may also be effected by the characteristics (e.g., power, torque, etc.) of the motor or other actuator that is responsible for generating the energy that results in movement of the percutaneous device. In various embodiments, catheter procedure system 10 is configured to provide for adaptable or adjustable control over the manner in which the percutaneous device is moved by catheter procedure system 10. In such embodiments, catheter procedure system 10 may be configured to provide for variability and user control over one or more of the factors that relate to the manner in which a percutaneous device is moved by catheter procedure system 10. Providing variability allows the movement of the percutaneous device by catheter procedure system 10 to be adjusted to suit the specific needs of a particular situation (e.g., particular types of percutaneous devices, different types of procedures, particular anatomy being navigated, the particular disease being treated, particular user preferences, etc.).

Figure 13:
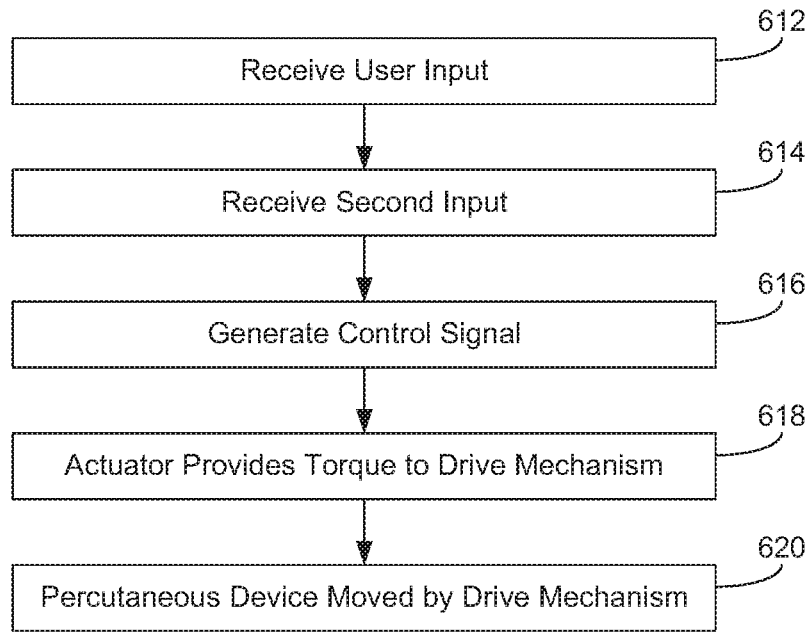
FIG. 13 is a flow diagram showing the function of a robotic catheter procedure system including variation and control of torque according to an exemplary embodiment.

In various embodiments, catheter procedure system 10 is configured to provide for the variation of the torque and/or rotational speed of an actuator, such as guide wire axial motor 602. FIG. 13 is a flow diagram generally showing control and variation of drive torque by catheter procedure system 10 according to an exemplary embodiment. At step 612, a user input is received, and at step 614 a second input is received. At step 616 a control signal is generated based on the user input and the second input, and the generated control signal is communicated to one of the actuators that provides torque to the drive mechanism of bedside system 12. The torque generated in response to the control signal by the actuator may be varied, controlled or limited as discussed herein. At step 618, the actuator provides torque to the drive mechanism based on the control signal, and at step 620 the percutaneous device is moved by the drive mechanism.

In some embodiments, procedure control module 98 and/or guide wire axial drive motor 602 may be configured to provide for variability and control of the axial force (i.e., the force directed along the longitudinal axis of guide wire 301 that results in advancement and retraction of guide wire 301) applied to guide wire 301 by drive wheel 410 during advancement and retraction of guide wire 301. Variability and control of the axial force applied to guide wire 301 may be desirable for various reasons including, providing improved ability to traverse a partial occlusion or chronic total occlusion (collectively referred to as "CTO"), etc. In various embodiments, variability and control of the axial force applied to guide wire 301 is achieved by varying the current and/or voltage supplied to guide wire axial drive motor 602 from power supply 606. This control of guide wire axial drive motor 602 acts to vary the rotational speed and/or torque that guide wire axial drive motor 602 imparts to guide wire 301 via capstan 306 and drive wheel 410.

In some embodiments, variation of current and/or voltage supplied to guide wire axial drive motor 602 from power supply 606 (and the corresponding variation in the rotational speed and/or torque that guide wire axial drive motor 602 imparts to guide wire 301) occurs in response to control signals 116 generated by procedure control module 98. Control signals 116 may be based upon a user input (e.g., the user's operation of controls 16) and based upon a second input (e.g., other information or data available to procedure control module 98, an additional user input, etc.), and the actuator may provide torque to a percutaneous device (e.g., the guide wire) via a drive mechanism in response to the control signal. Procedure control module 98 is described as being configured to control, limit, vary, etc. the torque provided an actuator, such as guide wire axial drive motor 602, based on various inputs (e.g., information, data, operating conditions, etc.) and/or based upon user inputs received by a user interface (e.g., controls 16). It should be understood that, in one embodiment, the functionalities provided by control module 98 discussed herein are provided by generating control signals 116 based upon the various inputs, and the control signals 116 are transmitted or communicated to an actuator (e.g., guide wire actuator 602). In this embodiment, the actuator then provides or generates a torque to a drive mechanism in response to the control signal.

During some intervention procedures, it is necessary that the guide wire traverse a partial or total occlusion of the coronary arteries. During these procedures, the guide wire must be advanced with enough axial force such that the guide wire pushes through the occlusion. However, once the guide wire is through the occlusion it may be desirable to reduce the amount of torque the motor provides to drive the guide wire. Thus, in various embodiments, guide wire axial drive motor 602 is a motor having torque and speed characteristics such that it provides increased torque during traversal of the occlusion. For example, in one embodiment, guide wire axial drive motor 602 is configured to deliver sufficient torque via its output shaft such that the axial force imparted to guide wire 301 is great enough to allow guide wire 301 to traverse a total occlusion. In another embodiment, guide wire axial drive motor 602 is configured such that the maximum torque that may be delivered via its output shaft is such that the axial force imparted to guide wire 301 is not sufficient to traverse the occlusion.

In another embodiment, guide wire axial drive motor 602 is selected to have a relatively low maximum output shaft speed (i.e., the no-load speed of the motor) to prevent sudden unwanted acceleration of guide wire 301. For example, the output speed of the motor shaft may be varied so as to not provide sufficient axial force to traverse the occlusion. This lower force may be useful when navigating the guide wire to the occlusion, or after the guide wire has traveled through the occlusion. A reduction in motor torque may be desirable once the guide wire has traversed an occlusion, such as a CTO, with guide wire 301. This will limit the guide wire from accelerating once the load of the occlusion has passed. This potential unwanted acceleration of guide wire 301 can be minimized by selecting a guide wire axial drive motor 602 with a low maximum output shaft speed or with a controller that controls the speed to a constant speed at a given input by the operator. For example, if the operator moves a joystick a certain distance from a neutral position, the speed will remain constant even if the torque is modified for a portion of the travel distance of the guide wire.

In other embodiments, procedure control module 98 is configured to control the voltage and/or current supplied to guide wire axial drive motor 602 by power supply 606 in order to control and vary the axial force applied to guide wire 301 by drive wheel 410 based upon a first user input and a second input. In one embodiment, procedure control module 98 is configured to limit the maximum speed and maximum torque supplied by guide wire axial drive motor 602 based upon an input indicative of the current location of the tip of the guide wire within the patient's vascular system. Thus, in this embodiment, control signal 116 generated by procedure control module 98 may be based upon information related to the location of the tip of the guide wire within the patient and based upon the user's operation of controls 16. For example, procedure control module 98 may be configured such that the maximum speed and/or maximum torque supplied by guide wire axial drive motor 602 is set higher when the tip of the guide wire is located with the large arteries (e.g., aorta, femoral artery, etc.) and the maximum speed and/or maximum torque supplied by guide wire axial drive motor 602 is set lower when the tip of the guide wire is located with the smaller arteries (e.g., coronary arteries, etc.). In such embodiments, procedure control module 98 may be configured to determine the information related to the location of the tip of the guide wire in various way. For example, procedure control module 98 may prompt the user to input the current location of the tip of the guide wire via controls 16 (e.g., touch screen 18), location of the guide wire tip may be determined by image processing of images captured via imaging system 32, or the location may be determined via the distance information captured by a guide wire axial motion sensor assembly, such as encoder assembly 406, discussed above.

In another embodiment, procedure control module 98 is configured to limit the maximum speed and/or maximum torque supplied by guide wire axial drive motor 602 based upon an input indicative of the type of movement being performed by the guide wire. Thus, in one embodiment, control signal 116 generated by procedure control module 98 may be based upon information related to the direction of movement of the guide wire and based upon the user's operation of controls 16. For example, procedure control module 98 may be configured such that the maximum torque and/or speed supplied by guide wire axial drive motor 602 is set lower when the guide wire is being advanced and the maximum torque and/or speed supplied by the guide wire axial drive motor 602 is set higher when the guide wire is being retracted. This arrangement may be desirable because blood vessel perforation may be less likely when the guide wire is being retracted.

In other embodiments, procedure control module 98 may be configured to control the torque and speed supplied by guide wire axial drive motor 602 to assist in traversal of an occlusion such as a CTO. Thus, in one embodiment, control signal 116 generated by procedure control module 98 may be based upon an input indicative of information related to whether the tip of the percutaneous device is traversing an occluded portion of a vessel of the patient's vascular system and based upon the user's operation of controls 16. For example, procedure control module 98 may be configured such that the maximum torque supplied by guide wire axial drive motor 602 is set higher and the maximum speed supplied by guide wire axial drive motor 602 is set lower during traversal of a CTO. In this embodiment, controls 16 (e.g., touch screen 18) may include a button that the user selects when occlusion or CTO traversal is about to start, and selection of the button by the user provides a user input that activates the occlusion or CTO traversal limits discussed above. In other embodiments, procedure control module 98 may determine that occlusion or CTO traversal is occurring by identifying the position of the guide wire relative to the occlusion or CTO from image information captured by imaging system 32. In another embodiment, procedure control module 98 may be configured to determine the extent of occlusion or CTO traversal that has occurred (i.e., how far through the occlusion or CTO the guide wire has traveled), and to control the torque and speed supplied by guide wire axial drive motor 602 based on the extent of occlusion or CTO traversal. For example, procedure control module 98 may be configured to decrease the torque supplied by guide wire axial drive motor 602 as the guide wire nears the end of the occlusion or CTO. In one such embodiment, the extent of occlusion or CTO traversal by the guide wire is determined from image information captured by imaging system 32.

In another embodiment, procedure control module 98 is configured to limit the maximum torque supplied by guide wire axial drive motor 602 such that the axial force imparted to guide wire 301 is low enough that guide wire 301 is capable of navigating through the blood vessels needed during a procedure at a proper force level. In one such embodiment, procedure control module 98 is configured with a set or non-variable maximum torque threshold such that the torque supplied by guide wire axial drive motor 602 remains below the threshold under all operating conditions. In this embodiment, the set or non-variable maximum torque threshold is selected such that the axial force applied to the guide wire is optimized for the type of blood vessel to be traversed during a particular procedure.

In another embodiment, procedure control module 98 is configured with a variable maximum torque threshold that is determined based upon various data or information accessible by procedure control module 98. In this embodiment, the torque supplied by guide wire axial drive motor 602 remains below the variable threshold during the procedure. In one such embodiment, the variable maximum torque threshold is determined from image data captured by imaging system 32. Thus, in this embodiment the maximum torque threshold may be determined based upon the thickness of the blood vessel walls at a certain location identified from the image data, and procedure control module 98 is configured to utilize the determined torque threshold to limit the maximum allowable torque of guide wire axial drive motor 602 as the guide wire traverses that portion of the blood vessel. In another embodiment, the maximum torque threshold utilized by procedure control module 98 is based upon the characteristics of the particular guide wire being used. For example, the maximum torque threshold may be set higher for a larger diameter guide wire than for a smaller diameter guide wire.

In another embodiment, procedure control module 98 may be configured to allow the user to set the maximum torque and maximum speed supplied by guide wire axial drive motor 602. In one embodiment, procedure control module 98 may display a button on touch screen 18 prompting the user to set the maximum torque and maximum speed. In another embodiment, controls 16 may include a set of controls (e.g., dials, sliders, etc.) allowing the user to set the maximum torque and maximum speed supplied by guide wire axial drive motor 602. In various embodiments, the user may be able to adjust the maximum torque and maximum speed as desired throughout the procedure.

In various embodiments, catheter procedure system 10 may be configured to limit the torque supplied by guide wire axial drive motor 602 to ensure that the supplied torque does not exceed a default maximum torque limit. In an embodiment in which guide wire axial drive motor 602 is an electric motor, procedure control module 98 may be configured to limit the amount of electrical current supplied to guide wire axial drive motor 602 by power supply 606 such that the torque supplied by guide wire axial drive motor 602 does not exceed the default maximum torque. The electrical current limit may be applied either via hardware or via computer code. In one such embodiment, procedure control module 98 may be programmed to include an electrical current limit, and procedure control module 98 may be configured to prevent the current delivered to guide wire axial drive motor 602 from exceeding the current limit.

Figure 14:
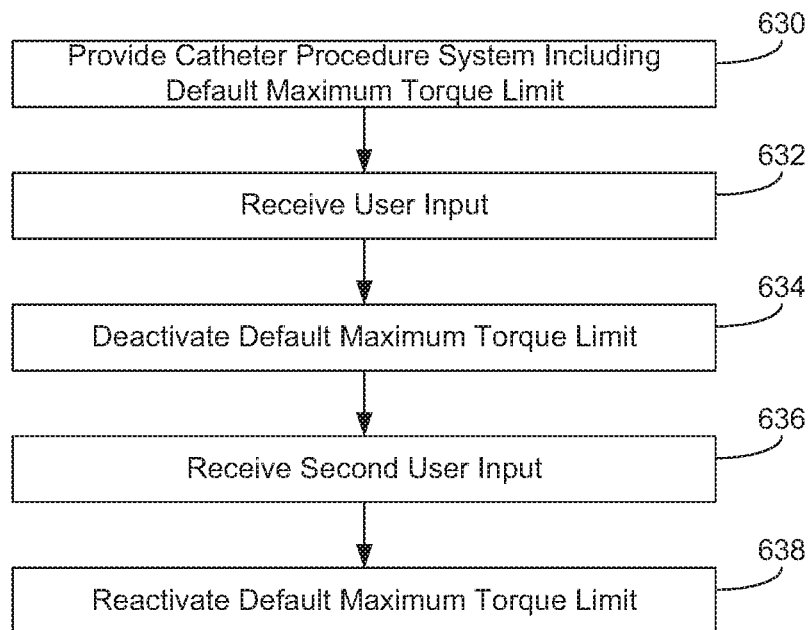
FIG. 14 is a flow diagram showing operation of a robotic catheter procedure system including a default maximum torque limit according to an exemplary embodiment.

In an embodiment including a default maximum torque as shown in FIG. 14, a catheter procedure system 10 may be provided that includes a default maximum torque limit at step 630. At step 632, a user input may be received, and, at step 634, the default maximum torque limit may be deactivated based on the received user input. In this embodiment, the user interface of catheter procedure system 10 may be configured to receive the user input that allows the user to deactivate the default maximum torque. In one such embodiment, an element of controls 16 (e.g., an icon displayed on touch screen 18 such as icon 162, 164 and 166) is configured to receive one or more user inputs to allow the user to deactivate and reactivate the default maximum torque threshold as desired. In this embodiment, the user may interact with the control element to deactivate the default maximum torque limit allowing the torque provided by guide wire axial drive motor 602 to exceed the default threshold. This embodiment may provide greater flexibility by allowing the user of catheter procedure system 10 to remove the default torque limit in situations where a greater torque is desired or needed. For example, the default maximum torque limit may be deactivated during particular types of procedures, while using different types of guide wires, while navigating various portions of the vascular system, etc.

In one embodiment, if the user has deactivated the maximum torque limit, at step 636 a second user input may be received, and, at step 638, the default maximum torque limit is reactivated in response to the second user input. In one such embodiment, the user may reactivate the default maximum torque limit by interacting with the control element to ensure that the torque provided by guide wire axial drive motor 602 does not exceed the default maximum limit. The user may reactivate the default maximum torque limit once the portion of the procedure that necessitated use of a higher torque is complete. In another embodiment, catheter procedure system 10 may be configured to automatically reactivate (e.g., to reactivate without the need for a specific user input) the default maximum torque limit. In one exemplary embodiment, procedure control module 98 is configured to automatically reactivate the default maximum torque limit when the user has stopped interacting with controls 16 to move a percutaneous device for a set period of time. In another embodiment, the default maximum limit may be reactivated prior to the start of a new procedure on a new patient.

In one embodiment, catheter procedure system 10 is configured to display information to the user at workstation 14 regarding whether the default maximum torque limit is currently active or is currently inactive. In one such embodiment, a separate icon (such as icon 162, 164 and 166) may be displayed via a display device of workstation 14 indicating the current status of the default maximum torque limit. In another embodiment, the control element for controlling activation and deactivation of the default maximum torque limit may be configured to provide an indication of the current status of the default max torque limit. For example, the control element may be a touch screen icon that assumes one color (e.g., gray) when the limit is inactive and another color (e.g., blue) when the limit is active.

In another embodiment, catheter procedure system 10 may include a default maximum torque limit, as discussed above, and a fixed or absolute maximum torque limit that may not be deactivated. In such an embodiment, the absolute maximum torque limit is greater than the default maximum torque limit and is selected to ensure that the torque supplied by guide wire axial drive motor 602 does not exceed the structural, safety or other limits of the guide wire or of the components of the bedside system. In one such embodiment, catheter procedure system 10 may be configured to allow the user to adjust or set the maximum torque limit to a maximum torque value between the default maximum torque limit and the absolute maximum torque limit. Once set, the torque limit set by the user will be applied by catheter procedure module 98 to ensure that the torque supplied by guide wire axial drive motor 602 does not exceed the set torque limit.

In some embodiments, the default maximum torque limit may be variable. For example, in some embodiments, the default maximum torque limit may be based upon one or more factor of a particular procedure that is being performed using catheter procedure system 10. For example, the default maximum torque may be based on the type of procedure being performed, the type of percutaneous device being moved by bedside system 12, the size of the vasculature that the percutaneous device is being navigated through, etc. This variability may help to ensure that the default maximum torque limit is set to a value that is desirable for the particular procedure that is being performed. Catheter procedure system 10 may be configured to automatically detect the factors needed to set the default maximum threshold for the procedure. In one embodiment, the type of percutaneous device that bedside system 12 is equipped with may be identified via a barcode or via an RFID tag associated with the percutaneous device, and the size of the vasculature may be determined by processing image data showing the vessels within which the device is being moved.

In one embodiment, bedside system 12 may include a sensor configured to determine the amount of axial force applied to guide wire 301 by guide wire axial drive motor 602 as guide wire axial drive mechanism 350 advances and retracts the guide wire. In another embodiment, procedure control module 98 may be configured to determine the amount of axial force applied to guide wire 301 by guide wire axial drive motor 602 as guide wire axial drive mechanism 350 advances and retracts the guide wire by monitoring the operating state of guide wire axial drive motor 602. In one embodiment, procedure control module 98 is configured to display information related to the determined amount of axial force to the user via a display device, such as monitors 26 and 28. For example, the display may be a bar display that fills in as axial force increases or a dial display with a needle that indicates the determined force. The display may also provide an indication of the axial force that would result in blood vessel perforation during the procedure. This indication may be a displayed force number or may be a graphical representation, such as a threshold line, displayed on the bar display discussed above. Procedure control module 98 may be configured to determine the axial force that would result in blood vessel perforation based on the location of the guide wire (e.g., in the aorta, in the coronary arteries, etc.) or this determination may be calculated from the image information of the patient's vascular system. For example, the image information may provide an indication of vascular wall thickness in the area in which the tip of guide wire 301 is located, and the wall thickness may be used to calculate the amount of force needed to puncture a vessel wall having that thickness.

In various embodiments, catheter procedure system 10 is configured to control and vary the amount of friction or drag that is applied to the percutaneous devices by bedside system 12 during movement of the percutaneous device. Movement of the percutaneous device by bedside system 12 can be altered by controlling the friction experienced by the percutaneous device. For example, the axial speed (e.g., speed of advancement or retraction) and rotational speed of a percutaneous device that results from a particular drive torque can be increased by decreasing the friction or drag experienced by the percutaneous device. Conversely, the axial speed (e.g., speed of advancement or retraction) and rotational speed of a percutaneous device that results from a particular axial drive torque can be decreased by increasing the friction or drag experienced by the percutaneous device.

Friction occurs between the percutaneous device and the drive mechanism wheels, and unneeded friction can be reduced by disengaging wheels that do not need to be engaged for the current movement of the percutaneous device. Accordingly, in one embodiment, bedside system 12 may be operated in at least a first drive mode to move the percutaneous device when one or more unneeded engagement structure is disengaged from the percutaneous device and a second drive mode.

In one embodiment, the first drive mode is an accelerated or "high speed" axial drive mode during which one or more non-axial drive wheels of bedside system 12 are disengaged from the guide wire to lower the drag on the guide wire, and the second drive mode is a nonaccelerated axial drive mode during which all of the non-axial drive wheels of bedside system 12 are engaged with the guide wire. Thus, while in the "high speed" axial drive mode, one or more of the non-axial drive wheels (e.g., roller wheels 430 and 442 of encoder assembly 406, and wheels 522 and 524 of rotational drive assembly 326) may be disengaged from the guide wire to reduce the friction on the guide wire. In the "high speed" axial drive mode, the guide wire will move axially at a faster speed and will accelerate faster for a given torque supplied by guide wire axial drive motor 602 when compared to a movement mode in which the non-axial drive wheels of bedside system 12 are engaged with the guide wire.

In one embodiment of a system operable in a "high speed" axial drive mode, catheter procedure system 10 is configured to disengage the engagement structure (e.g., wheels 522 and 524 shown in FIG. 10) of the rotational drive assembly from the guide wire when bedside system 12 is to be operated in "high speed" axial drive mode. In this embodiment, as shown in FIG. 12, bedside system 12 may include a disengagement actuator 608 located within motor drive base 302 that is configured to cause disengagement of the wheels of guide wire rotational drive mechanism 380 when bedside system 12 is to be operated in the high speed axial mode. Further, controls 16 may include one or more control element (e.g., a touch screen icon such as icon 162, 164 and 166) configured to receive user inputs that allow the user to activate and deactivate the high speed mode. When the "high speed" mode control element is activated, a control signal 116 is transmitted to disengagement actuator 608 triggering activation of disengagement actuator 608 which in turn causes disengagement of the of the engagement structure of the rotational drive assembly from the guide wire. When the "high speed" mode control element is deactivated, a control signal triggers deactivation of disengagement actuator 608 which in turn causes reengagement of the engagement structure of the rotational drive assembly with the guide wire.

In one exemplary embodiment, the engagement structure of the rotational drive assembly includes several sets of pairs of wheels 522 and 524 as shown in FIGS. 9 and 10. As discussed above regarding FIG. 9 and FIG. 10, wheels 522 and 524 may be moved from the engaged position (FIG. 9) to the disengaged position (FIG. 10) by the application of an axial force to base plate 544. The axial force causes wheels 524 to pivot away from wheels 522 such that the outer surfaces of wheels 522 and 524 no longer contact guide wire 301. As shown in FIG. 12, bedside system 12 may include a structure 610 that is moved by disengagement actuator 608 to apply the axial force to base plate 544. In one embodiment, structure 610 is a pair of rods or arms that extend from the upper surface of motor drive base 302 and are positioned adjacent to base plate 544.

When the user activates "high speed" axial drive mode, actuator 608 moves the two arms of disengagement structure 610 laterally (parallel to the upper surface of the motor drive base 302) to engage the outer surface of base plate 544 and to apply the axial force to base plate 544 to disengage wheels 522 and 524 from guide wire 301. With wheels 522 and 524 disengaged from guide wire 301 the friction or drag on the guide wire is decreased which allows the guide wire to be moved axially at a faster speed for a particular drive motor torque.

In one embodiment, dedicated guide wire control 23 (FIG. 1) is a joystick type control. In this embodiment, the electric current delivered to guide wire axial motor 602 from power supply 606 is a function of the degree of displacement of the joystick, and the torque supplied by guide wire axial motor 602 is a function of the delivered electric current. In this embodiment, for a particular displacement of the joystick control (e.g., a particular user input), a given or predetermined torque will be supplied to guide wire axial drive mechanism 350 from guide wire axial motor 602. Thus, in the "high speed" axial mode, the speed of guide wire 301 for given the predetermined torque will be greater than the speed of guide wire 301 for the same torque when the engagement structure of the rotational drive mechanism is engaged. Further, in one embodiment, catheter procedure system 10 sets a maximum for the electrical current supplied to guide wire axial motor 602, and, in this embodiment, the maximum speed of the guide wire is greater when bedside system 12 is operating in "high speed" mode than when bedside system 12 is operating in the regular mode.

When "high speed" axial mode is no longer needed or rotational movement is desired, a control element of controls 16 is actuated by the user to deactivate "high speed" axial mode. When controls 16 receive the input from the user indicating that the system is be moved from "high speed" mode to regular mode, the two arms of disengagement structure 610 are moved away from base plate 544 disengaging disengagement structure 610 from the surface of base plate 544 allowing wheels 522 and 524 to reengage guide wire 301 as discussed above. With wheels 522 and 524 engaged with guide wire 301, bedside system 12 is then operated in the non-high speed or regular axial drive mode.

As noted above, the user may manually toggle between "high speed" and non-high speed axial drive modes by interacting with a control element of controls 16. Because shortening procedure time is often advantageous, the user may select to operate bedside system 12 in "high speed" mode in a number of situations. In particular, the user may select "high speed" axial drive mode to perform those portions of the procedures in which slow, precise movements are not necessary. For example, high speed axial drive mode may be selected by the user when the guide wire is moving through large blood vessels and/or during retractions of the guide wire after the procedure is completed.

In another embodiment, catheter procedure system 10 may be configured to operate in a "high speed" rotational drive mode. Similar to the embodiments discussed above, in this embodiment, the engagement structure of the guide wire axial drive mechanism may be disengaged from the guide wire. With the friction experienced by the guide wire reduced, the rotational drive mechanism can rotate the guide wire at a faster speed or acceleration. In one such embodiment, the "high speed" rotational drive mode may be selected to facilitate rotation of the guide wire during traversal of an occluded portion of the patient's vascular system.

In some embodiments, controller 40 (e.g., via assist module 102) may be configured to provide a suggestion to the user located at workstation 14 regarding whether operating in "high speed" mode is recommended, desirable, etc. In one such embodiment, the suggestion may be based upon various information available to controller 40. For example, procedure control module 98 may determine the diameter of the blood vessel that the tip of the guide wire is in from imaging data, and if the diameter is greater than a predetermined threshold, procedure control module 98 may display a suggestion to the user that "high speed" mode may be enabled.

In other embodiments, controller 40 may be configured to limit those situations in which the user may activate "high speed" mode. For example, in one such embodiment, if the determined diameter of the blood vessel is less than a predetermined threshold, control module 98 may be configured to prohibit the activation of high speed mode by the user. In this embodiment, the control for activating "high speed" mode may be configured to provide an indication regarding whether "high speed" mode is available. For example, the control for activating "high speed" mode may be a touch screen icon (such as icon 162, 164 and 166) that may be displayed in a first color (e.g., grey) when "high speed" mode is not available and a second color (e.g., green) when "high speed" mode is available.

Figure 15:
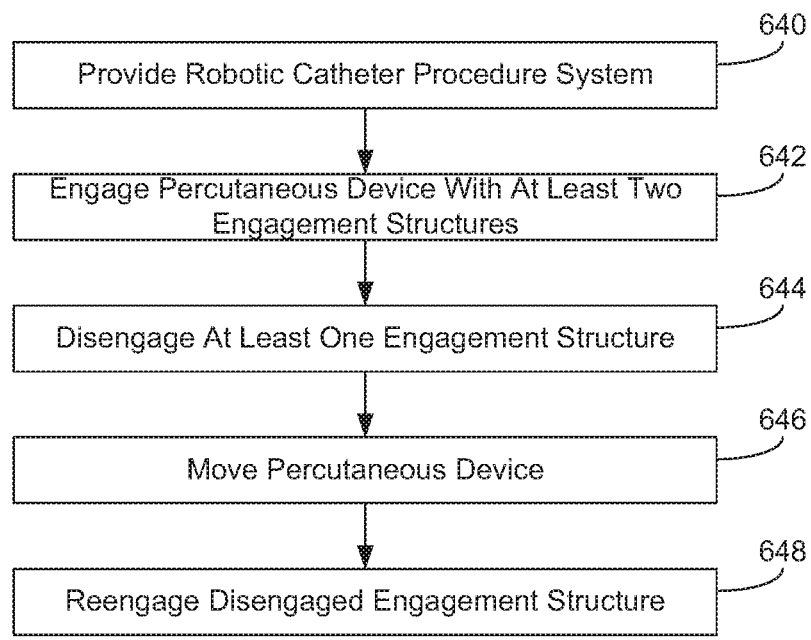
FIG. 15 is a flow diagram showing operation of a robotic catheter procedure system to limit friction or drag on a percutaneous device according to an exemplary embodiment.

Referring to FIG. 15, a method of operating a robotic catheter procedure system is shown according to an exemplary embodiment. At step 640, a robotic catheter procedure system, such as the various embodiments of catheter procedure system 10 discussed above, is provided. At step 642, the percutaneous device is engaged by at least two engagement structures of the robotic catheter system (e.g., an engagement structure of an axial drive mechanism and an engagement structure of a rotational drive mechanism). This engagement may result from control signals 116 generated by user interaction with controls 16, as discussed above. At step 644, one of the engagement structures is disengaged from the percutaneous device. This disengagement may result from a control signal 116 generated by the user via interaction with controls 16. At step 646, the engaged drive mechanism is operated to move the percutaneous device while the other engagement mechanism remains disengaged. The movement of the percutaneous device may result from a control signal 116 generated by the user via interaction with controls 16 as discussed above. At step 648, the disengaged engagement structure may be reengaged with the percutaneous device. The reengagement of the engagement structure may result from a control signal 116 generated by the user via interaction with controls 16 as discussed above.

In various embodiments, catheter procedure system 10 may be configured to control or vary the amount of friction experienced between the engagement structure of the drive mechanism and the percutaneous device. For example, in one embodiment, catheter procedure system 10 may be configured to control or vary the amount of friction experienced between wheels 410, 418, 430 and 442 of guide wire axial drive mechanism 350 (shown in FIG. 6) and guide wire 301.

As discussed above regarding FIG. 6, springs 424 and 436 exert a force to bias wheels 418 and 430 to engage guide wire 301 between wheels 410 and 442, respectively. In one such embodiment, the normal force applied to guide wire 301 by wheels 410, 418, 430 and 442 generated by springs 424 and 436 (e.g., the pinch force) may be variable or controllable allowing for control of the friction between the wheels 410, 418, 430 and 442 and guide wire 301.

In various embodiments, the pinch force may be varied to accommodate the use of a variety of different types of guide wires. For example, if cassette 300 is equipped with a guide wire having a rough or textured outer surface, the pinch force generated by springs 424 and 436 may be decreased to ensure the proper amount of friction between the wheels and the guide wire. In contrast, if cassette 300 is equipped with a guide wire having a smooth outer surface, the pinch force generated by springs 424 and 436 may be increased to ensure the proper amount of friction between the wheels and the guide wire. In other embodiments, the pinch force may be controlled to vary the performance of cassette 300 during a procedure. For example, the pinch force may be increased to help ensure that the guide wire remains in place (i.e., no axial motion occurs) when the controls for guide wire axial motion are not being actuated by the user and/or when the user is actuating controls for a different percutaneous device.

The pinch force may be varied or controlled by the user in various ways. For example, in one embodiment, cassette 300 may include one or more actuators, shown as spring force actuator 650 in FIG. 12, configured to adjust or vary the force generated by springs 424 and 436 in response to a control signal received from controller 40. Referring to FIG. 6, in one embodiment, spring 424 is mounted at one end to wheel housing 420 and at the other end to mounting block 652, and spring 436 is mounted at one end to wheel housing 432 and at the other end to mounting block 654. In this embodiment, spring force actuator 650 may be a motor, such as a step motor, that engages mounting blocks 652 and 654 via a coupling element 656 and moves mounting blocks 652 and 654 toward guide wire 301 to increase the force generated by springs 424 and 436 and that moves mounting blocks 652 and 654 away from guide wire 301 to decrease the force generated by springs 424 and 436.

Controls 16 may include a control (e.g., a button, dial, touch screen icon, etc.) that allows the user to alter the pinch force of guide wire axial drive mechanism 350 from workstation 14. In another embodiment, controller 40 may be configured to automatically adjust the pinch force generated by springs 424 and 436 based upon the type of guide wire that cassette 300 is equipped with. Controller 40 may prompt the user to identify the type of guide wire via controls 16 (e.g., via a drop down menu, scanning a bar code, etc.). In another embodiment, catheter procedure system 10 may be configured (e.g., bedside system 12 may be equipped with a transceiver) to automatically identify the type of guide wire that cassette 300 is equipped with (e.g., via reading of an RFID tag associated with the guide wire), and controller 40 may be configured to automatically control the pinch force based on the automatically determined guide wire type.

In another embodiment, catheter procedure system 10 may include a sensor that detects slippage between the wheels of guide wire axial drive mechanism 350 and guide wire 301. Slippage may be detected in various ways including using an optical sensor to monitor actual movement of guide wire 301, using an encoder or other sensor to monitor the actual movement of one of the wheels or by monitoring the current drawn by guide wire axial motor 602. In this embodiment, data from the slippage sensor is received and analyzed by controller 40, and if controller 40 detects that slippage is occurring, a control signal is generated and communicated to spring force actuator 650 to increase the force applied by spring 424 and/or spring 436 to wheel 418 and/or wheel 430, depending on where slippage was detected. Slippage may be overcome in this manner because the friction between guide wire 301 and wheels of guide wire axial drive mechanism 350 increases as the pinch force generated by springs 424 and 436 increases. In another embodiment, catheter procedure system 10 may be configured to determine whether the pinch force between the wheels of guide wire axial drive mechanism 350 and guide wire 301 is higher than needed and to reduce the pinch force accordingly.

It should be understood that, in various embodiments, catheter procedure system 10 may include one or more of any of the various variable force and variable speed concepts discussed above, in any combination, to provide for additional variability in control of the percutaneous device. For example, catheter procedure system 10 may be configured to control or vary both the torque supplied by guide wire axial motor 602, and the normal force applied to guide wire 301 by the wheels of guide wire axial drive mechanism 350. This embodiment may provide for useful control over the movement of the percutaneous device. In one such embodiment, if high axial force is needed (e.g., to traverse a CTO), catheter procedure system 10 may be configured to increase the torque generated by guide wire axial motor 602 to generate the higher axial force needed to push through the CTO and to increase the normal force generated by spring 424 using actuator 650, as discussed above, to accommodate the transmission of higher force to guide wire 301 without slippage.

In another embodiment, catheter procedure system 10 may be configured to control the normal force applied to guide wire 301 to induce slippage between drive wheel 410 and guide wire 301 as a mechanism for ensuring the axial force applied to guide wire 301 remains below a certain threshold. In this embodiment, the normal force can be controlled to ensure that slippage between drive wheel 410 and guide wire 301 occurs if guide wire axial motor 602 attempts to impart an axial force exceeding the frictional force between drive wheel 410 and guide wire 301. In one such embodiment, if high axial speed but low maximum potential axial force is needed, catheter procedure system 10 may be configured to control guide wire axial motor 602 at a relatively fast rotational speed and to decrease the normal force generated by spring 424 using actuator 650, as discussed above. In this mode of operation, if the guide wire encounters an obstacle and guide wire axial motor 602 attempts to deliver an axial force greater than the frictional force, drive wheel 410 will slip over guide wire 301 instead of continuing to push guide wire 301 into the obstacle. In one such embodiment, because slippage of this nature is indicative of an obstacle, controller 40 may be configured to detect such slippage and to automatically stop guide wire axial drive motor 602 to allow the user to evaluate the cause of the obstruction. Further, controller 40 may be configured to display a warning message or icon to the user at workstation 14 indicating that an obstacle has been encountered.

In various embodiments, controller 40 and working catheter axial drive motor 600 may be configured to provide for variability and control of the speed and axial force applied to working catheter 303 by drive wheel 458 during advancement and retraction of working catheter 303. Controller 40 and working catheter axial drive mechanism 352 may also be configured to provide for variability and control over the normal force applied to working catheter 303 by drive wheel 458 and roller 466 during advancement and retraction of working catheter 303. In one such embodiment, bedside system 12 may include a spring force actuator that adjusts the force imparted to roller 466 by a spring associated with working catheter axial drive mechanism 352. Variability and control of the axial force applied to working catheter 303 may be desirable for various reasons, including lowering the risk of blood vessel perforation, providing improved ability to traverse a partial occlusion or chronic total occlusion (CTO), specific control of different types of working catheters, etc. It should be noted that, while the above disclosure relates primarily to variable control of the forces and speed imparted to a guide wire by guide wire axial drive motor 602 and the wheels and springs of the related engagement structures, the same variable force and speed concepts may be applied to control of working catheter 303 and/or working catheter axial drive motor 600.

Further modifications and alternative embodiments of various aspects of the invention will be apparent to those skilled in the art in view of this description. Accordingly, this description is to be construed as illustrative only. The construction and arrangements, as shown in the various exemplary embodiments, are illustrative only. While the current application recites particular combinations of features in the claims appended hereto, various embodiments of the invention relate to any combination of any of the features described herein whether or not such combination is currently claimed, and any such combination of features may be claimed in this or future applications. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A robotic catheter procedure system, comprising:
    a bedside system, the bedside system comprising:
        a percutaneous device;
        a drive mechanism configured to engage and to impart an axial force to the percutaneous device; and
        an actuator providing torque to the drive mechanism to impart the axial force to the percutaneous device; and
    a remote workstation, the remote workstation comprising:
        a user interface configured to receive a first user input; and
        a control system operatively coupled to the user interface, the control system configured to communicate a control signal to the actuator, the control signal based upon the first user input and a second input, wherein the second input comprises information related to the percutaneous device;
    wherein the actuator provides torque to the drive mechanism in response to the control signal, wherein the actuator is inhibited from delivering torque exceeding a default maximum torque limit,
    wherein the control system is configured to deactivate the default maximum torque limit based on the second input, wherein the actuator is permitted to deliver torque exceeding the default maximum torque limit when the default maximum torque limit is deactivated, and wherein the control system is configured to reactivate the default maximum torque limit when no user input is received for a predetermined period of time.

2. The robotic catheter procedure system of claim 1, wherein the control system is configured to further reactivate the default maximum torque limit when a new procedure is started.

3. The robotic catheter procedure system of claim 1, wherein the user interface is configured to receive a second user input, wherein the control system is configured to deactivate the default maximum torque limit based on the second user input, wherein the actuator is permitted to deliver torque exceeding the default maximum torque limit when the default maximum torque limit is deactivated, and further wherein the user interface is configured to receive a third user input, wherein the control system is configured to reactivate the default maximum torque limit based on the third user input.

4. The robotic catheter procedure system of claim 1, wherein the torque provided by the actuator is variable.

5. The robotic catheter procedure system of claim 1, wherein the second input comprises information related to the direction of movement of the percutaneous device, and further wherein the torque provided by the actuator in response to the control signal is greater when the percutaneous device is being retracted than when the percutaneous device is being advanced.

6. The robotic catheter procedure system of claim 1, wherein the second input comprises information related to the location of the tip of the percutaneous device within the vascular system of a patient.

7. The robotic catheter procedure system of claim 6, wherein the torque provided by the actuator in response to the control signal is decreased when the tip of the percutaneous device is located in a coronary artery of the patient.

8. The robotic catheter procedure system of claim 6, wherein the information related to the location of the tip of the percutaneous device within the vascular system of a patient is determined from image data received from an imaging system.

9. The robotic catheter procedure system of claim 1, wherein the second input comprises information related to whether the tip of the percutaneous device is traversing an occluded portion of a vessel of the patient's vascular system, and further wherein the torque provided by the actuator in response to the control signal is increased when the tip of the percutaneous device is traversing the occluded portion of the vessel.

10. The robotic catheter procedure system of claim 9, wherein the percutaneous device is a guide wire.

11. The robotic catheter procedure system of claim 1, wherein the actuator is an electric motor.

12. The robotic catheter procedure system of claim 11, wherein the torque delivered by the electric motor is varied by varying at least one of the current and the voltage supplied to the electric motor by a power supply, and wherein at least one of the current and voltage is varied based upon the control signal.

13. The robotic catheter procedure system of claim 11, wherein the percutaneous device is a guide wire, and further wherein the torque provided by the actuator in response to the control signal is sufficient to allow the guide wire to traverse an occluded portion of a vessel of the patient's vascular system.

14. The robotic catheter procedure system of claim 1, wherein the drive mechanism comprises:
    a first wheel; and
    a second wheel;
        wherein the percutaneous device is positioned between the first wheel and the second wheel, wherein the first wheel and the second wheel move toward each other to apply a normal force to the outer surface of the percutaneous device; and
        wherein the normal force is variable.

15. The robotic catheter procedure system of claim 14 further comprising a second actuator actuator that applies a force to the first wheel to increase the normal force.

16. The robotic catheter procedure system of claim 15, wherein the drive mechanism includes a spring that biases the first wheel toward the percutaneous device, wherein the second actuator is configured to expand and to compress the spring to control the force the spring exerts on the first wheel.

17. The robotic catheter procedure system of claim 16, wherein the first wheel is a roller wheel and the second wheel is an opposing drive wheel.

18. The robotic catheter procedure of claim 14, wherein the second input is information related to the normal force applied to the percutaneous device by the first and second wheels.

19. A system for operating a robotic catheter system having a drive mechanism configured to engage and to impart an axial force to a catheter device and to advance and retract the catheter device and an actuator configured to deliver torque to the drive mechanism, the system comprising:

a user interface configured to receive a first user input;

a control system operatively coupled to the user interface configured to generate a control signal, the control signal based upon the first user input, wherein the actuator delivers torque to the drive mechanism to move the catheter device in response to the control signal; and a default maximum torque limit, wherein the actuator is inhibited from delivering torque exceeding the default maximum torque limit, wherein the control system is configured to deactivate the default maximum torque limit based on a second input, wherein the actuator is permitted to deliver torque exceeding the default maximum torque limit when the default maximum torque limit is deactivated, and wherein the control system is configured to reactivate the default maximum torque limit when no user input is received for a predetermined period of time.

* * * * *